United States Patent
Calderwood

(10) Patent No.: US 11,759,154 B2
(45) Date of Patent: Sep. 19, 2023

(54) BARRIER-CONTAINED RADIOLOGICAL SENSOR HOLDER

(71) Applicant: Mitchell C Calderwood, Fernandina Beach, FL (US)

(72) Inventor: Mitchell C Calderwood, Fernandina Beach, FL (US)

(*) Notice: Subject to any disclaimer, the term of this patent is extended or adjusted under 35 U.S.C. 154(b) by 0 days.

(21) Appl. No.: 17/751,434

(22) Filed: May 23, 2022

(65) Prior Publication Data

US 2023/0090890 A1 Mar. 23, 2023

Related U.S. Application Data

(63) Continuation-in-part of application No. 16/350,420, filed on Nov. 15, 2018, now Pat. No. 11,337,664.

(51) Int. Cl.
*A61B 6/14* (2006.01)
*A61B 46/17* (2016.01)
*A61B 6/00* (2006.01)

(52) U.S. Cl.
CPC .............. *A61B 6/145* (2013.01); *A61B 6/425* (2013.01); *A61B 46/17* (2016.02)

(58) Field of Classification Search
CPC ......... A61B 6/145; A61B 6/425; A61B 46/17; A61B 6/4423; A61C 19/00
See application file for complete search history.

(56) References Cited

U.S. PATENT DOCUMENTS

| | | |
|---|---|---|
| 4,426,716 A | 1/1984 | Muether |
| 4,810,194 A | 3/1989 | Snedden |
| 6,030,119 A | 2/2000 | Tachibana |
| 6,520,676 B1 * | 2/2003 | Schmitz ................. G03B 42/06 378/191 |
| 6,540,399 B1 | 4/2003 | Eppinger |
| 6,688,766 B2 | 2/2004 | Gant |
| 6,811,312 B2 | 11/2004 | Bratslavsky |
| 7,004,627 B2 | 2/2006 | Strong |
| 7,070,326 B2 | 7/2006 | Manley |
| 7,090,395 B2 | 8/2006 | Glazer |

(Continued)

FOREIGN PATENT DOCUMENTS

| | | |
|---|---|---|
| WO | WO 02/40082 A2 | 5/2002 |
| WO | WO 02/40082 A3 | 5/2002 |

*Primary Examiner* — David P Porta
*Assistant Examiner* — Mamadou Faye
(74) *Attorney, Agent, or Firm* — Gordon E. Gray, III; GRAY LAW FIRM

(57) ABSTRACT

The present invention is an improved barrier-contained radiological sensor holder. In particular, the present invention is directed to radiological sensor holder contained in a barrier sheath to reduce or prevent contamination. The radiological sensor holder preferably comprises a sensor holder at least partly contained within a barrier sheath having a closed end and an open end. The barrier sheath preferably comprises elastomer latex material and the sensor holder preferably comprises an exterior attachment and an interior container, where the exterior attachment presses a portion of the barrier sheath into a gapped attachment port on the interior container. The sensor holder may alternately include an expansion slit along the opposing face. The sensor holder can also have snap on articles for positioning the sensor for posterior, anterior and vertical image capture.

18 Claims, 24 Drawing Sheets

(56) References Cited

U.S. PATENT DOCUMENTS

| | | |
|---|---|---|
| 7,097,356 B2 | 8/2006 | Calderwood |
| 7,261,463 B2 | 8/2007 | Becht |
| 7,309,158 B2 | 12/2007 | Halevi |
| 7,517,148 B2 | 4/2009 | Ceisel |
| 7,661,880 B2 | 2/2010 | Calderwood |
| D624,189 S | 9/2010 | Rutt |
| 8,500,328 B2 | 8/2013 | Frampton |
| 8,602,646 B2 | 12/2013 | Frampton |
| 8,641,276 B2 * | 2/2014 | Abramovich ........ A61B 6/4423 378/38 |
| 9,351,692 B2 | 5/2016 | Yao |
| 9,642,583 B2 | 5/2017 | Yao |
| 9,643,355 B2 | 5/2017 | Frampton |
| 9,986,955 B2 | 6/2018 | Heo |
| 2002/0103462 A1 | 8/2002 | Nesbitt |
| 2005/0259791 A1 * | 11/2005 | Strong ................. G03B 42/042 378/168 |
| 2006/0245549 A1 | 11/2006 | Calderwood |
| 2009/0136003 A1 | 5/2009 | Gestetner |
| 2011/0017619 A1 * | 1/2011 | Motoyama ........... A61B 6/4423 206/305 |
| 2012/0213337 A1 | 8/2012 | Gestetner |
| 2014/0349245 A1 | 11/2014 | Gestetner |
| 2015/0282772 A1 | 10/2015 | Winters |
| 2018/0028131 A1 | 2/2018 | Brenner |
| 2018/0028132 A1 | 2/2018 | Brenner |
| 2019/0038248 A1 | 2/2019 | Martelon |

\* cited by examiner

US 11,759,154 B2

BARRIER-CONTAINED RADIOLOGICAL SENSOR HOLDER

This application is a continuation in part application of U.S. patent Ser. No. 16/350,420, which is incorporated herein by reference in its entirety.

TECHNICAL FIELD

The present invention is an improved barrier-contained radiological sensor holder. In particular, the present invention is directed to radiological sensor holder contained in a barrier to reduce or prevent contamination.

BACKGROUND ART

Digital radiological sensors generally fall into two categories: CMOS (complementary metal oxide semiconductor) and CCD (charge-coupled device). Each utilizes scintillators to convert x-rays into visible light. The sensitivity of these sensor chips generally does not allow for heat or chemical sterilization. Dental practitioners are required by the U.S. Food and Drug Administration to maintain these small, very expensive digital radiological sensors in a clean and un-contaminated state for use between patients. Pathogens should not be allowed to cross contaminate patients during any radiological procedure.

Current systems for maintaining oral radiological sensors in an uncontaminated state require the dental practitioner to first insert the sensor into a barrier. Barriers are typically made from flexible polyethylene plastic, elastomeric latex or nitrile rubber. All of these materials provide generally sufficient barriers. However, it is often difficult and time consuming to insert a sensor into a barrier as barriers should be tight fitting to the sensor. A tightly fitted barrier reduces the incidence of artifacts in resultant radiological images and reduces the incidence of choking reactions from patients. Even a small amount of excess barrier material protruding from the distal end of the sensor can cause a choking reaction.

Typically, the second step for the practitioner prior to capturing a radiological image with the sensor is to place the barrier-covered sensor into a sensor holder/positioner so that the sensor can be placed at the proper angle and position in the patient's oral cavity to capture the preferred image. An example of a sensor holder/positioner is shown in U.S. Pat. No. 6,520,676. This patent is incorporated herein by reference in its entirety.

Sensors come in a variety of sizes and shapes and therefore, consequently, a variety of holders are available as well. However, sensors fitted with a barrier in different manufacturer's holders can present problems with slack space, too tight a fit, additional handling time. This can also result in movement of sensor during image capture, damage to the sensor and additional time for the practitioner inserting the sensor. Additionally, a third item is often applied to cushion the holder and sensor so it does not irritate soft tissue in a patient's oral cavity. Accordingly, a device is needed that aids a dental practitioner in maintaining oral radiological sensors (regardless of size) in an uncontaminated state from patient to patient while providing a sensor positioning means for image capture and doing so in a more time efficient and cost-effective way than is currently available.

SUMMARY OF THE INVENTION

The present invention is an improved barrier-contained radiological sensor holder. In particular, the present invention is directed to radiological sensor holder contained in a barrier sheath to reduce or prevent contamination. The radiological sensor holder preferably comprises a sensor holder at least partly contained within a barrier sheath having a closed end and an open end. The barrier sheath preferably comprises elastomer latex material and the sensor holder preferably comprises an exterior attachment and an interior container, where the exterior attachment presses a portion of the barrier sheath into a gapped attachment port on the interior container. The sensor holder may alternately include an expansion slit along the opposing face. The sensor holder can also have snap on articles for positioning the sensor for posterior, anterior and vertical image capture.

BRIEF DESCRIPTION OF THE DRAWINGS

The objects and features of the present invention, which are believed to be novel, are set forth with particularity in the appended claims. The present invention, both as to its organization and manner of operation, together with further objects and advantages, may best be understood by reference to the following description, taken in connection with the accompanying drawings.

DETAILED DESCRIPTION OF THE PREFERRED EMBODIMENTS

The following description is provided to enable any person skilled in the art to make and use the invention and sets forth the best modes contemplated by the inventor of carrying out his invention. Various modifications, however, will remain readily apparent to those skilled in the art, since the general principles of the present invention have been defined herein specifically to provide an improved barrier-contained radiological sensor holder.

To insert a prior art sensor holder/positioner by hand into any given barrier is difficult and time consuming Often, the positioner itself may not fit properly within a given barrier. This would likely render its positioning qualities useless and can compromise the cross-contamination integrity of any given barrier with tiny holes or obvious damage to the thin barrier material itself from, e.g. forcing the holder to inside the barrier. Therefore, hand insertion is not practical or not recommended in a clinical setting.

Figure 1:
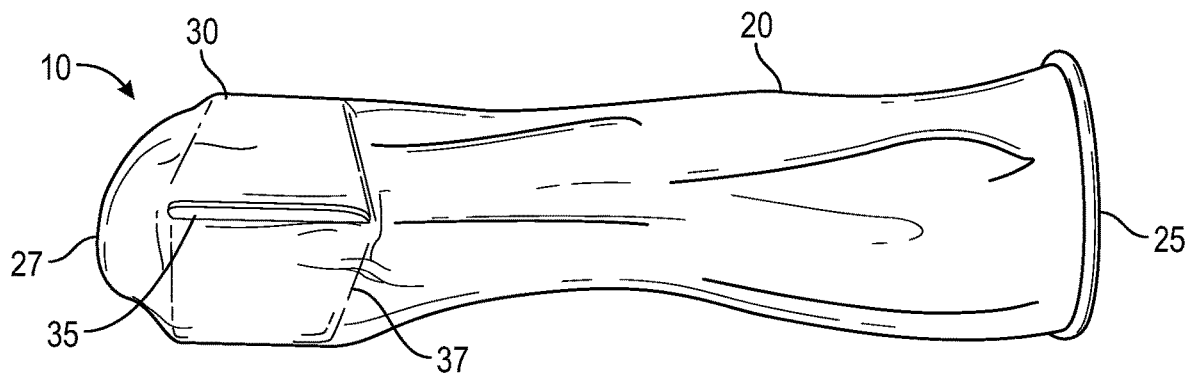
FIG. 1 is a top perspective view of a preferred embodiment of the invention.
Figure 3:
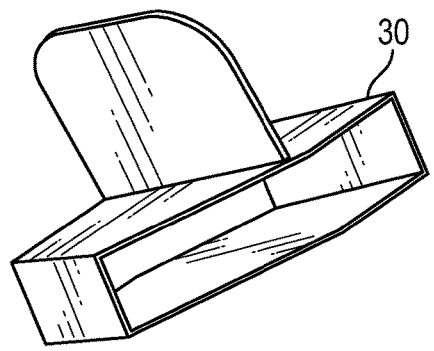
FIG. 3 is a side perspective view of a preferred embodiment of the sensor holder.

Referring now to FIG. 1, a top view of a preferred embodiment of the invention 10 is shown. A barrier sheath 20 is shown encapsulating a sensor holder 30. The barrier sheath 20 is preferably 0.1 mm to 4 mm in thickness. The sensor holder 30 preferably comprises a bitewing 35 and a sensor compartment 37. As shown, the holder 30 is located inside the barrier sheath 20 as opposed to prior art devices where holders/postioners are located external to the barrier. Referring now to FIG. 3, a preferred embodiment sensor holder 30, such as one described in U.S. Pat. No. 6,520,676, is shown without a barrier sheath 20. Preferably, a sensor holder is 1"×1.25" in size.

The combination of holder 30 and barrier 20 can be produced to be disposable (single use) or sterilizable (multiple use). A sterilizable version is preferably produced from materials that could withstand repeated sterilization cycles at temperatures up to 190° C. such as acrylonitrile butadiene styrene (ABS), nylon (polyamide heat stabilized) or polypropylene.

Preferably, to assemble the present invention 10, a holder/positioner 30 is manufactured first then a barrier sheath 20 is applied using one of three preferred methods: 1) dipping; 2) molding; or, 3) spraying.

Figure 6:
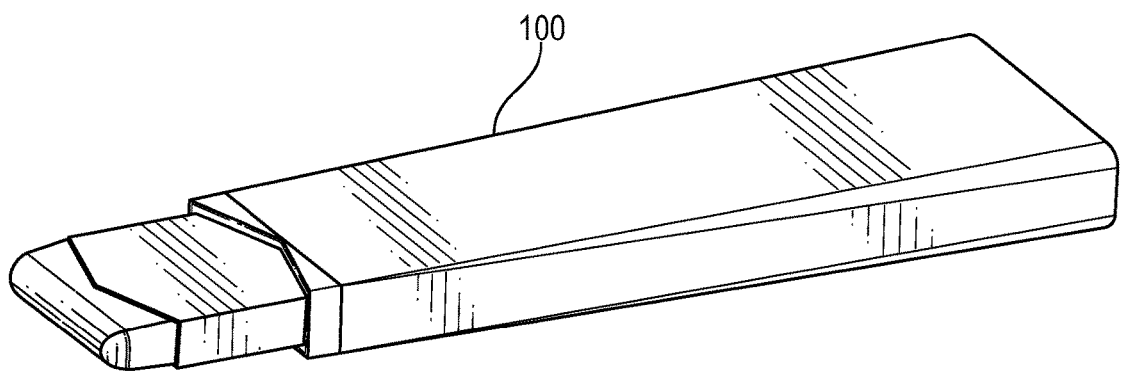
FIG. 6 is a side perspective view of preferred embodiment of a former alone.

Dipping Method:

A preferred method is "dipping" the sensor holder 30. Preferably, to encapsulate any given sensor holder 30 within an elastomer latex material such as, natural rubber latex or a synthetic elastomer such as nitrile, silicone, isoprene, etc., it will, in general, involve affixing the positioner/holder 30 to a dipping former (a preferred embodiment of a former 100 is shown in FIG. 6) that would be dipped into the elastomer latex and subsequently dried or cured in an oven or UV cured and then harvested. The primary difficulty in producing a suitable finished product is adhesion of the elastomer to the surface of the holder 30. Preferably, the holder 30 comprises a base material that promotes a low surface tension and has innate anchoring qualities such that the liquid elastomer will adhere to the holder and not flow off, "fish eye" or otherwise be repelled by the base material. A preferred material for the holder 30 is plastic. This could be any number of polymers including, but not limited to, polyethylene, polypropylene, thermo-plastic urethanes, foamed styrenes, foamed urethanes, silicones and/or blends of various polymers. In the case of most plastics, however, adhesion and anchoring are more difficult than pulp-based materials described below. Polymers generally present very smooth surfaces and surface energies that do not promote the adhesion of elastomers. Accordingly, surface treatments for the holder 30 are generally required when plastics are used. Preferred surface treatments include gamma ray treatment, electron beam treatment, flame treatment, chemical etching, or the use of various surface penetrates or coatings.

Alternative, yet also preferred, materials for the holder are wood, bamboo or bagasse (sugar cane) pulp based materials. These materials while porous can be molded, die cut and conformed into suitable holder shapes with good anchoring and adhesion properties that could be over dipped.

Figure 4:
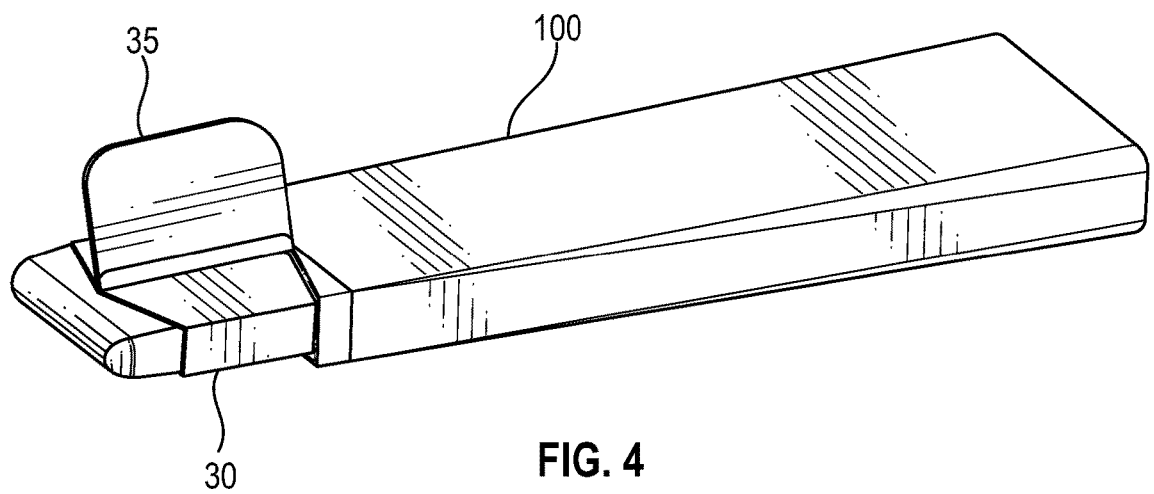
FIG. 4 is a side perspective view of a preferred embodiment of a sensor holder mounted on a former.
Figure 5:
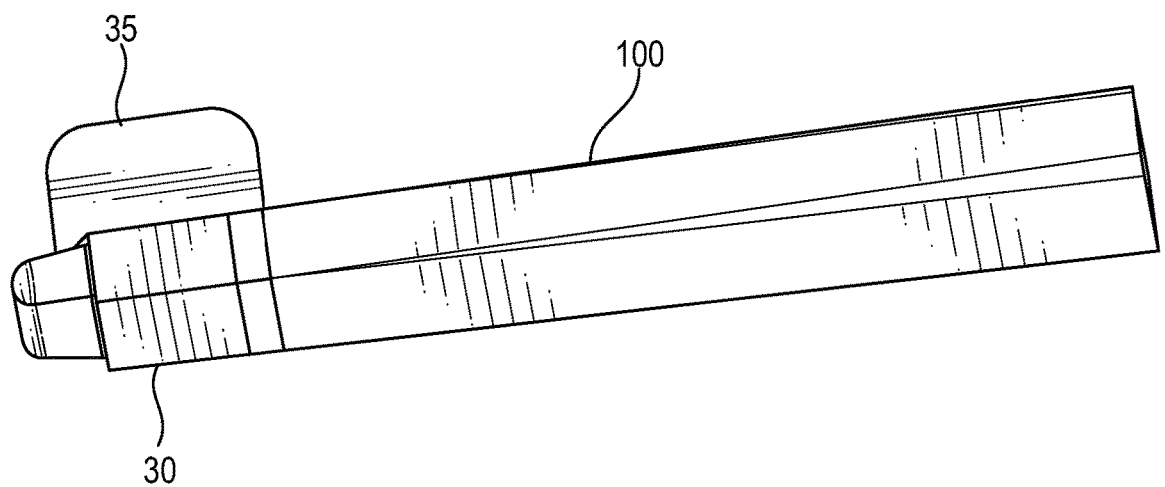
FIG. 5 is a side view of a preferred embodiment of a sensor holder mounted on a former.

Spraying Method:

The spraying method is another preferred method for encapsulating or partially encapsulating a sensor holder 30. Referring now to FIGS. 4-6, holders 30 would be attached to formers 100 during the spraying method of encapsulation. FIGS. 4 and 5 show a preferred embodiment of a holder 30 mounted on a preferred embodiment former 100. FIG. 6 shows a preferred embodiment former 100 alone. During a preferred spraying method, holders 30 and formers 100 would preferably transit a spray booth during which an elastomer would be applied in coats over the holders 30 and then cured. Curing is preferably by heat drying, gas, water, or chemical (catalyst) curing, or UV curing. A suitable adhesion and anchoring base material as described above for the holder 30 would also be necessary for this method. If an area of the holder 30, such as the bite wing 35, is not to be encapsulated by the sheath 20, that portion of the holder 30 can be covered to present elastomer from being sprayed thereon. Potentially, any elastomer can be used in the spraying method as long as the elastomer can be formulated into a spray-able viscosity. For example, an elastomer with a viscosity exceeding 3000 centipoise can become difficult to spray and there can be problems with running material, e.g. drips. On the other hand, dipping into a material of such a viscosity presents fewer drawbacks.

Plastic Film Encapsulation:

Holders 30 could be encapsulated within various plastic films such as polyethylene, polypropylene, polyvinylidene chloride (Saran), elastic polymer films, etc. These films could be heat-sealed or heat shrunk around various holders. However, this is not a preferred method, as more prior work would be needed in cutting and assembling a patchwork of pieces together around the holder. In addition, this method would lend itself to small and microscopic holes that could compromise the barrier integrity against pathogens. Encapsulation can be accomplished by spraying, dipping, heat-shrinking or even painting.

Injection Molding:

The molding method is also a preferred method for encapsulating holders 30 with barrier sheaths 20. Preferably, holders 30 are inserted into a tooling mold (not shown). The tooling mold is preferably made specifically for plastic or film injection molding and over molded. This method could be done on a single cavity or multi cavity injection mold. The mold molds the barrier sheath 20 surrounding the holder 30 and through heat and compression causes the barrier sheath material to weld to the holder's surface. The preferred elastomer for this method is liquid silicone rubber ("LSR"). A moving core in the mold is preferably used to prevent barrier material from filling unwanted areas. However, it should be noted that this method of production could have unfavorable processing drawbacks such as warped plastic holders from secondary, over mold temperatures that could create increased rates of rejected product. Also, there could be shrinkage problems between two differing materials. These could create increased rates of rejected product as well.

Barrier Coverage of the Sensor Holder:

The sensor holder 30 will, preferably, have one or two openings present to allow insertion of the sensor (not shown). Some prior art holders have movable parts as well. The preferred barrier sheath 20 has a single opening 25 for insertion of the sensor (not shown). However, the holder 30 as shown in FIG. 3 has two openings for insertion of the sensor. This allows a user to slide the sensor into the holder 30 via the barrier opening 25 and center the sensor in the holder 30 for proper location vis a vis the bite wing or bite surface 35 of the holder 30 for more precise image capture. Preferably, the bite wing or bite surface 35 is positioned by the user between the teeth of a patient where the desired image is needed. The barrier sheath 20 is preferably formed around the sensor holder 30 opposite the opening 25 such that a sensor has enough room to be centered in the holder 30. Therefore, the barrier sheath 20 preferably extends beyond the holder 30 forming a bubble 27 of protective barrier material encapsulating an end of the invention 10. The barrier sheath 20 preferably encapsulates the bite wing or bite surface 35 as shown in FIG. 1.

Figure 2:
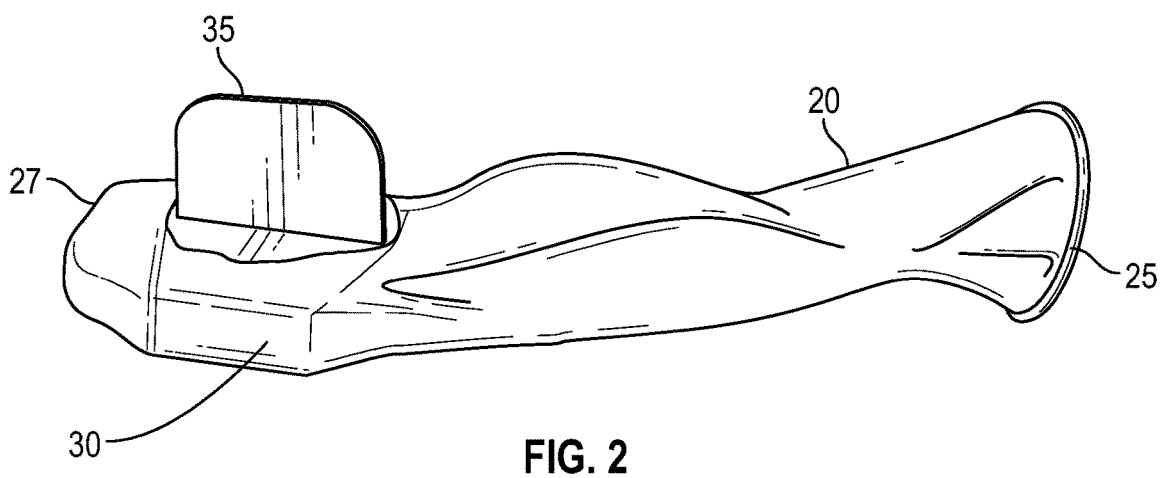
FIG. 2 is side perspective view of an alternative preferred embodiment of the invention.

Alternatively, the sheath 20 can seal via adherence and surface anchoring to the holder 30 such that the bite wing or bite surface 35 or some portion thereof is exposed outside the barrier sheath 20 as shown in FIG. 2. Thus, the sensor would still be encapsulated within the barrier sheath 20 and holder 30. This approach allows, for example, the bite surface 35 to be free of any barrier sheath material so that bite properties such as those disclosed in U.S. Pat. No. 6,520,676 can be seen and/or otherwise utilized.

The use of such an encapsulated sensor holder will allow for quicker and easier image capturing at a reduced cost in the clinical setting. Currently, using prior art devices, the practitioner must first apply a barrier to the sensor to prevent cross-contamination. Moreover, many patients also require the application of extra cushioning inside the barrier along the edges of the sensor as the edges can cause patient discomfort in soft tissue located in the roof of the mouth. Next, the sensor, enclosed within a barrier and likely padded as described, must be placed into a sensor holder in such a manner that it is secure and will not move during imaging. The practitioner then places the sensor and holder in a patient's oral cavity.

With the present invention, a practitioner preferably inserts the sensor through the open end 25 of the barrier 20 into the holder 30 and positions the holder 30 in a patient's oral cavity. The barrier 20 positioned on the outside of and surrounding the holder 30 provides additional cushioning for soft tissue as well as providing the needed pathogen barrier. Moreover, the barrier 20 contains the holder 30 to provide stability for the sensor during imaging within a patient's oral cavity.

Figure 7:
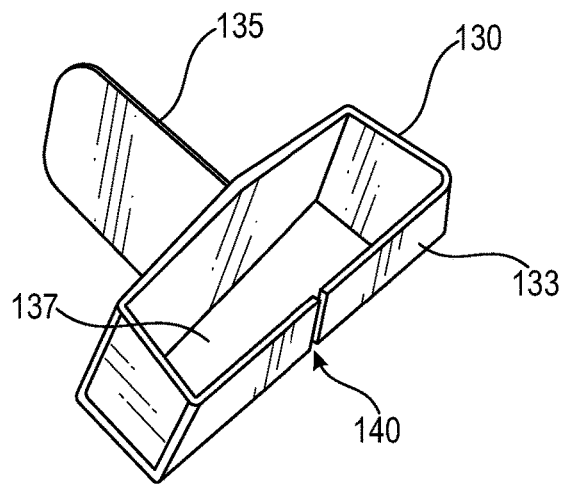
FIG. 7 is a top perspective view of an alternative embodiment of a sensor holder with an expansion slot.
Figure 8:
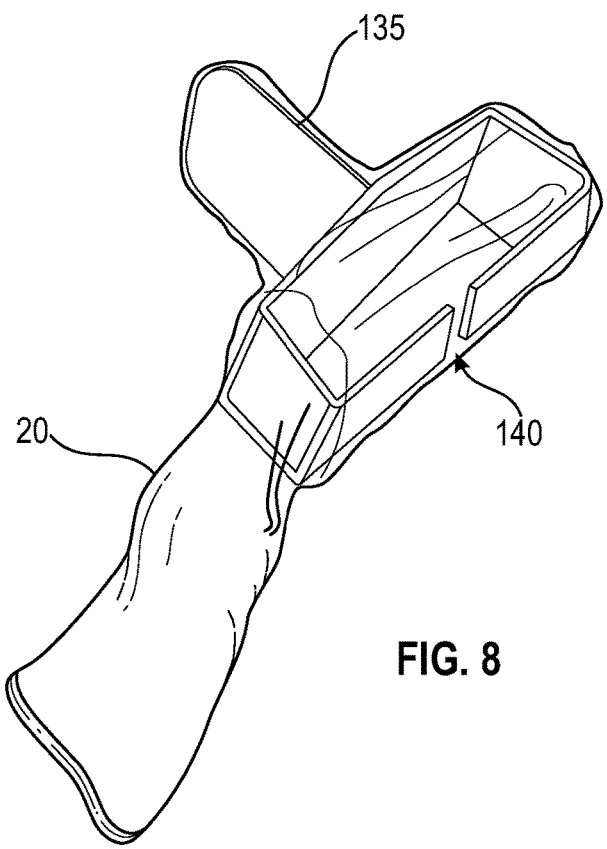
FIG. 8 is a top perspective view of an alternative embodiment of a sensor holder with an expansion slot in a barrier sheath.

An alternative embodiment of the sensor holder described above can also be used in this invention. As shown in FIGS. 7 and 8, an alternative embodiment sensor holder 130 is shown. In particular, opposite of bite wing 135 is opposing face 133 surrounding sensor compartment 137. Opposing face 133 has an expansion slot 140 running along opposing face 133. The expansion slot 140 allows the sensor compartment 137 to expand to accept larger sensors. The elastomeric encapsulation of the sheath 20, with sufficient durometer and elongation, will hold sensors of various sizes firmly in the sheath 20 and sensor holder 130 under lateral expansion of the sheath 20 to allow successful capture of clinical quality radiographic images. (Preferably, the elongation is between 400 and 1000% and durometer is from 20 Shore 00 to 30 Shore D.)

Alternative Embodiment

Referring now to FIGS. 9-22, alternative embodiments of the present invention are shown. These alternative embodiments allow for improved construction and manufacturing.

Preferably, a sensor holder is retained within a barrier generally made of a flexible, thin plastic or a thin elastic material such as natural rubber to prevent contamination from patient saliva, blood, infectious disease and materials utilized by a dentist in the oral cavity. Moreover, radiological sensors are expensive, delicate and are damaged easily by heat sterilization. Therefore, a one-time use, disposable barrier is preferred for every procedure. There are a multitude of positioning systems in use currently in dentistry for radiological sensors that are used by a clinician to obtain needed radiological images for diagnosis or procedure. However, prior art systems do not contain the sensor holder or its attachments within a barrier. Instead, the sensor is placed within the barrier and any positioning equipment, e.g. a sensor holder, is exterior to the barrier. These alternative embodiments can be manufactured as a single use, disposable device or can be produced from various materials as a re-usable device that can be sterilized. These alternative embodiments preferably comprise a sensor holder within the barrier but also have additional exterior attachments that allow a manufacturer to produce devices faster and with less product rejection and confirmed barrier integrity.

Manufacturing a device that has both an effective infectious disease barrier and an internal part made of plastic or other material presents several problems. For example, if the device has protruding, angular parts or attachments, those parts generally must either exit an opening at one end of a barrier or exit through a wall of the barrier or be tightly adhered to or welded to the inner surface of the barrier. If the barrier, regardless of the barrier's material, is not either snuggly fitted to the internal positioning device or internally attached to the surface of the device, the device may move within the barrier during use causing unacceptable images for the clinician or producing slack barrier material that can cause a gag reflex in the patient or overall patient discomfort. Producing a barrier that is form-fitting to the internally contained device is problematic. Prior art choices are limited and in general fall into three categories: adhesive bonding, heat welding or injection over molding. Adhesive bonding generally entails using solvent-based adhesives to make an effective bond between dissimilar materials. An adhesive bond will also be subject to moisture as well as heat and cold detachment, thus reducing product shelf life. Additionally, the use and reclamation of solvent-based adhesives can be a dangerous fire hazard, worker health hazard, air pollutant and/or expensive.

Heat welding, while generally not possible with natural rubber latex, may be possible with various more expensive synthetic elastomers depending what material the internal device is made of. However, heat welding is not ideal in manufacturing as it requires high energy use and the possibility of high rejection rates due to improper bonding and micro holes created in the thin films from which barriers are made. Generally, barrier film plastic or elastic barriers range from 0.001 to 0.004 inches thick. Barriers with higher wall thickness can add to patient gag reflex problems. Also, heat sources can easily melt through plastic barrier films quickly, often microscopically, and allow pathogens to transit the barrier via capillary pressure to a patient's oral cavity. Such micro holes are difficult to detect, and test for, on a per unit basis in manufacturing.

Over molding is a known plastic processing technique used in high speed, plastic injection molding. Generally, a prior made plastic part is placed in a mold, the mold is closed and a thin space is left around the part where a barrier can be molded around the part, e.g. from liquid silicone or a flowable plastic. The part is then cooled and removed from the mold. The part is thus contained within a form-fitting barrier. In general, the drawbacks for this approach include a substantially higher cost per unit, barrier wall thickness limitations (not less than 0.05) and choice of material limitations.

To avoid the problems described above, a manufacturer may choose, instead, to simply place a hole through the barrier, pass through any protruding portion of a sensor holder needed for positioning and then attach the barrier to the sensor holder and seal the barrier around and onto the internal sensor holder. This may be attempted with two of the techniques already described above, namely adhesive bonding or heat welding. Over molding would not be a candidate. In addition to the step described above for adhesive bonding or heat welding, a hole must be accurately placed in the barrier and then the internal piece must be either precision registered to pass through the pre-cut hole or a hole must be precision cut in the material above the protruding part so that it can pass through. Both of these steps are highly susceptible to failure in high-speed manufacturing. In addition, if a flap of material is present from the cut hole, it must be removed. Moreover, while cutting some barrier materials is not difficult, others such as elastomeric materials can be challenging.

The present invention allows for the production of a sensor holder within a snuggly-fitting barrier or other flexible containment material while still allowing for a protruding part, such as a bitewing. Preferably, in the present invention, a protruding part, such as a bite wing (that is utilized to capture periapical, radiological images), is outside of the barrier as a separate part and can be conjoined to the sensor holder inside the barrier via a male part extension on the protruding part that snap into a female side channel on the sensor holder with the barrier or containment material trapped in the channel between the two parts. The female side channel or male part extension can be on either of the parts, e.g. interchangeable, as long as one part is internal and one part is external to the barrier. For continuity of the description herein, the female side channel will be integral to the sensor holder located within the barrier or containment material.

In the manufacturing process, the internal part, e.g. sensor holder, would preferably be located at the end of a barrier. The second part, e.g. bitewing, preferably forms a right angle to the internal part, e.g. sensor holder. For example, a bite wing is preferably positioned external to the barrier and push snapped into the female side channel by hand or with a hydraulic, air or electro-activated roller forcing the male part extension down into the female side channel with the barrier material trapped between the two parts. Preferably, space is available between the male part extension and the female side channel to allow the barrier to reside within the channel while the male part extension is inserted therein. This space is dimensioned to approximate the wall thickness of the barrier. The barrier material, if elastic, would preferably deform to a thinner wall once the snap pressure was applied and the space available would range from 0.001 to 0.010 inches. The female side channel could be made in a multitude of ways, so long as the two pieces join and/or snap together firmly and can capture the barrier material between the two parts.

In addition to providing a fixed exterior part, such as a bitewing or bite surface, a secondary fixture such as an attachment means for other positioning fixtures can be located exterior to the barrier and fixed to the internal sensor holder in the same manner as the bitewing device described above. For example, the secondary attachment fixture could provide a means of snapping on and off other exterior positioning tools or sliding them on and off. The secondary attachment fixture could include a bitewing surface as described above as well. This type of attachment fixture could have more than one location on the barrier surface, several points on one side or several points on various surfaces of the interior sensor holder (ie. top, sides, ends, etc.). With such a device, a user could employ a bite surface or a bite block that can be moved during a radiological procedure around the surface of the sensor and utilized to obtain what is referred to, in the vernacular, as a "full mouth x-ray" or "F.M.X." For example, positioning the bite block on one side edge of the sensor holder on an "image capture" surface side of the sensor, would allow for an upper left and lower right posterior image to be obtained of a patient's side or distal teeth. Moving the bitewing block to the opposite side of the sensor "image capture" surface edge would allow for the upper right and lower left posterior images to be obtained. Moving the bite block to the narrow end of the sensor image capture side, would allow a user to obtain an anterior image of the patient's front teeth.

The present invention preferably has additional unique features. For example, the sensor holder has an interior container, preferably with a port, e.g. oval-shaped, for accepting an aimer ring extension device. This port can be round, square or any of a multitude of shapes, so long as it allows for a snug and stable fit between the two parts. An aimer ring is generally used as a guide by a user to properly align an x-ray source with the sensor so that the radiological image is on center as opposed to having a cut corner, elongation or other unacceptable image. The port is preferably located inside the barrier as opposed to outside the barrier on the exterior attachment. This allows the aimer ring arm to remain uncontaminated by a bio burden produced by the patient and thus, if handled correctly by a user during a procedure, eliminates the need to sterilize the aimer ring between each patient, a time and energy consuming step in patient care.

A second preferred feature of the interior container is an expansion slit or separation located opposite an attachment point for the exterior attachment. This preferably corresponds to a non-image capture side of the radiological sensor where a data cable attachment area exiting many sensors is located. This slit, or division, allows for the sensor holder to expand so that various sizes of sensors can be located within the interior container. When located within an elastic barrier, elastic pressure is sufficiently exerted against this slit in interior container to contain the sensor in a stable manner Stability against movement of the sensor is critical for obtaining proper, desirable, radiological images of any kind.

Figure 9:
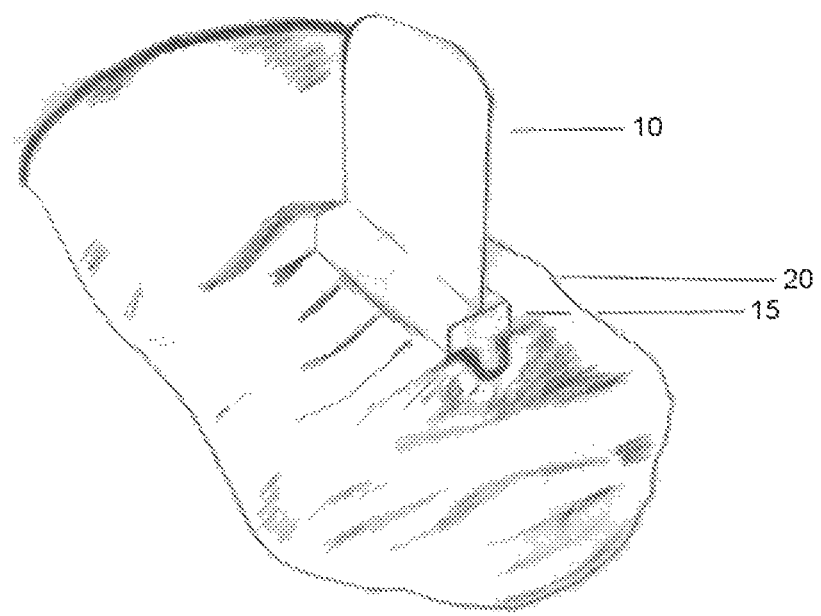
FIG. 9 is a perspective view of an alternative embodiment of a sensor holder in a barrier sheath.

Referring now to FIG. 9, a perspective view of a preferred embodiment is shown. An exterior attachment 10 with a male attachment point 15 is shown pressed against a barrier 20 and snapped into a gapped attachment port (not shown) on an interior container (not shown) within the barrier sheath 20.

Figure 10A:
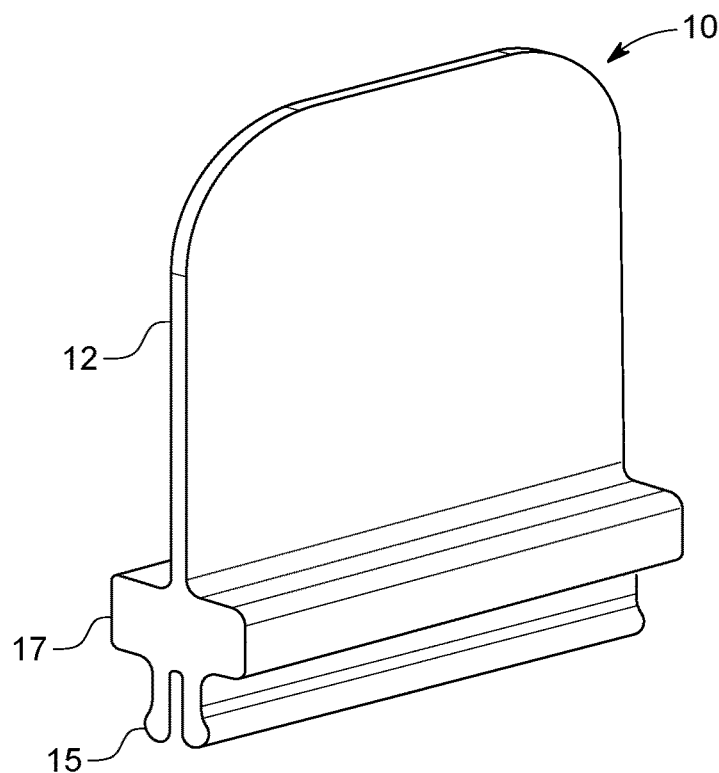
FIG. 10A is a side perspective view of an alternative embodiment of an exterior attachment.
Figure 10B:
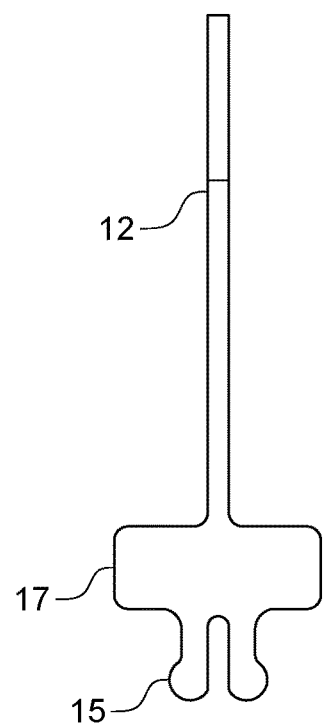
FIG. 10B is an end view of the embodiment in FIG. 10A.
Figure 10C:
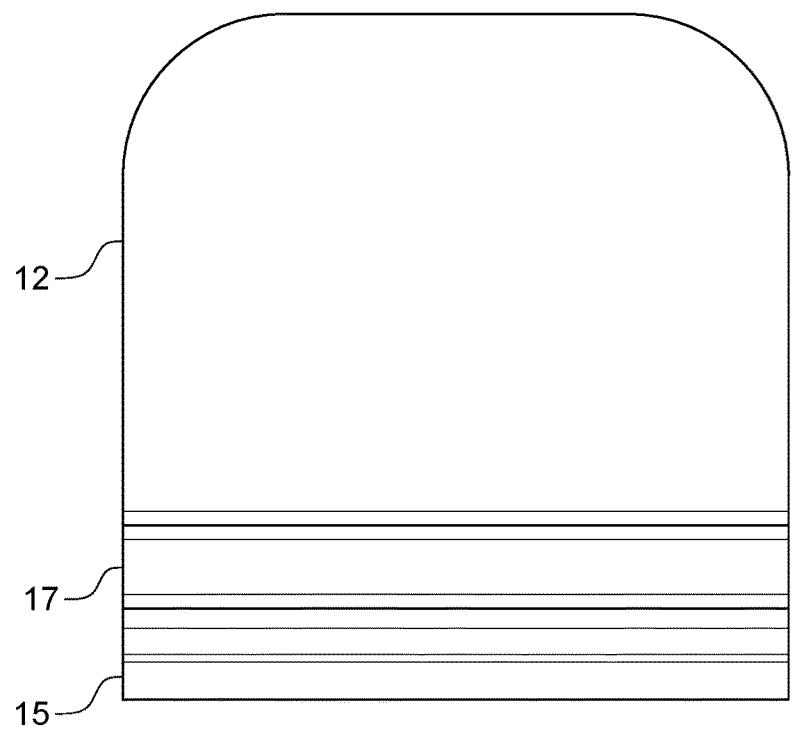
FIG. 10C is a side view of the embodiment in FIG. 10A.

Referring now to FIG. 10A, the exterior attachment 10 is shown as a bitewing 12 with a male attachment point 15. One of the preferred embodiments of the male attachment point 15 is shown in FIGS. 10A-10C as a flexible fork. The bitewing 12 is preferably thinner than a stabilizing block 17 between the bitewing 12 and the male attachment point 15.

Figure 11:
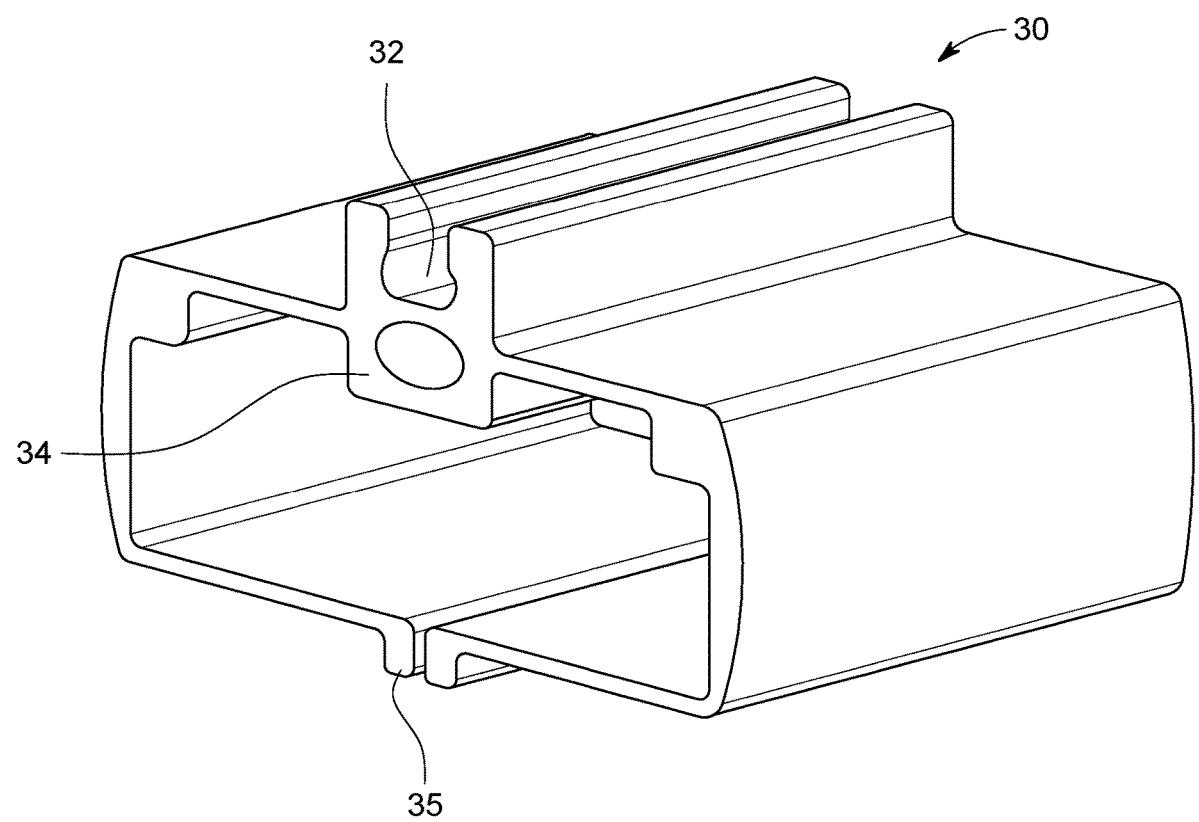
FIG. 11 is a side perspective view of an alternative embodiment of a sensor holder.

Referring now to FIG. 11, a perspective view of a preferred embodiment of an interior container 30 is shown. The interior container 30 preferably comprises a gapped attachment port 32 sized to receive, and hold securely, the male attachment point 15 and a portion of a barrier sheath 20. As shown, the interior container 30 preferably further comprises a port for an aimer ring 34. Furthermore, the interior container 30 preferably comprises an expansion slit 35 located opposite the gapped attachment port 32.

Figure 12A:
FIG. 12A is a side view of an alternative embodiment of an exterior attachment.
Figure 12B:
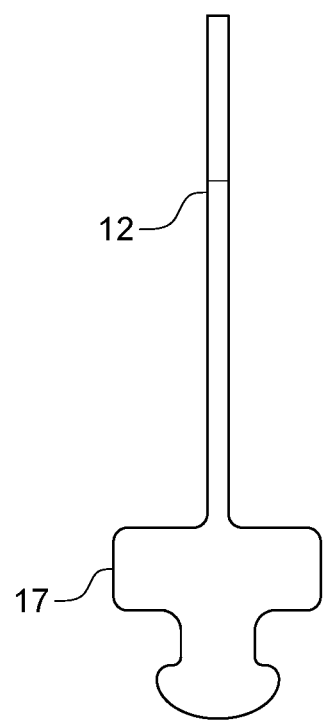
FIG. 12B is an end view of an alternative embodiment of an exterior attachment.
Figure 13A:
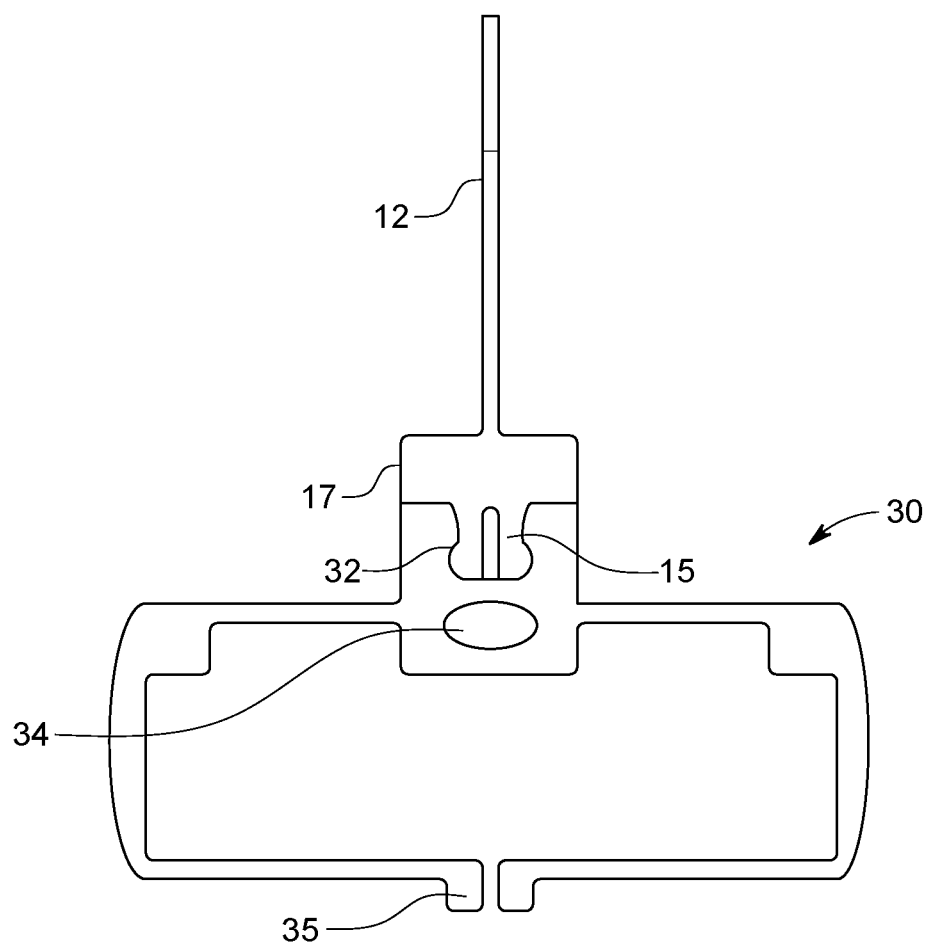
FIG. 13A is a side view of an alternative embodiment of the invention.
Figure 13B:
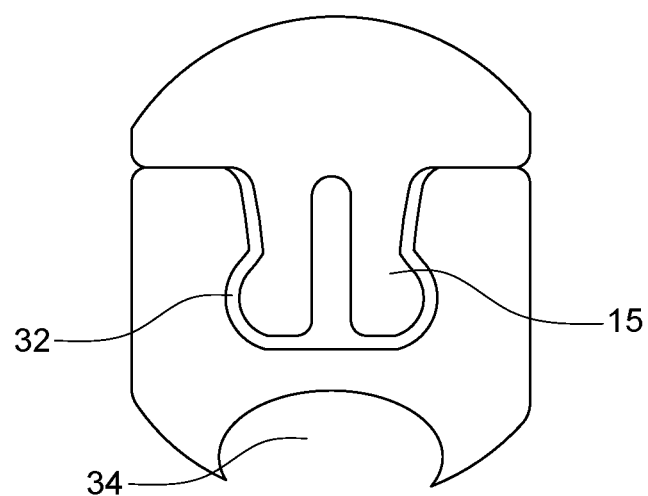
FIG. 13B is a partial side view of an alternative embodiment of the invention.
Figure 14A:
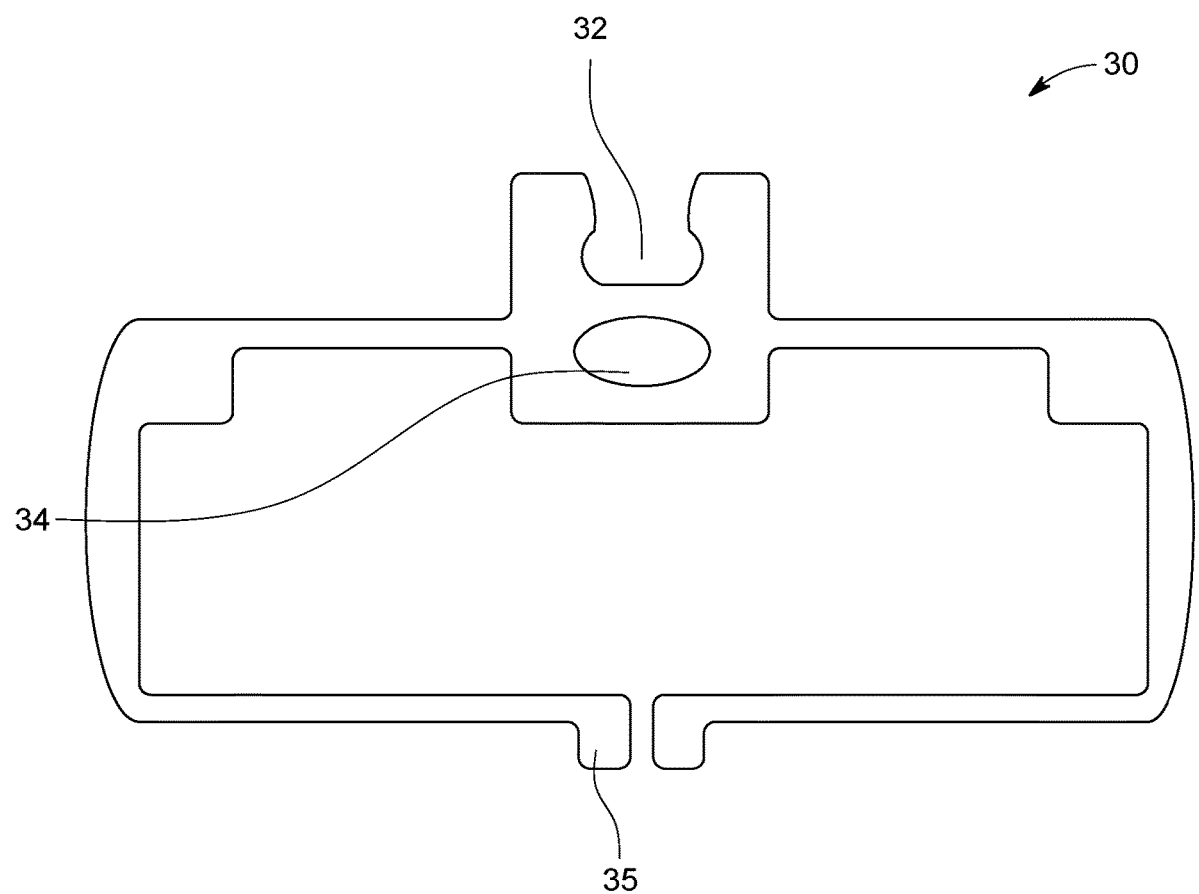
FIG. 14A is a side view of the alternative embodiment in FIG. 11.
Figure 14B:
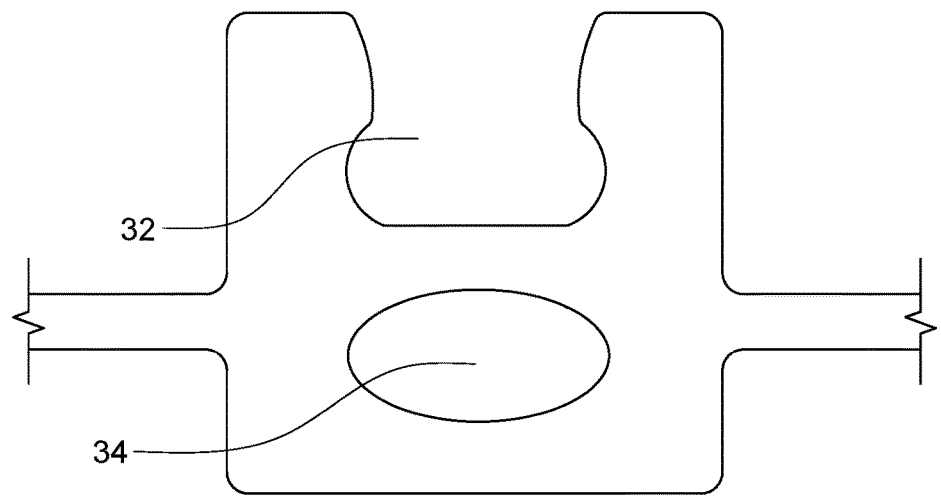
FIG. 14B is a partial side view of FIG. 14A.

Referring now to FIGS. 12A and 12B, an alternative embodiment of the exterior attachment 10 is shown. Rather than the flexible fork male attachment point 15 of FIG. 10A, a rounded male attachment point 15 is shown. Preferably, either version of male attachment point 15 can be inserted into the gapped attachment port 32 as shown in FIGS. 13A-13B and 14A-14B, respectively. For clarity, these figures are shown without the barrier sheath 20 in place.

Figure 15A:
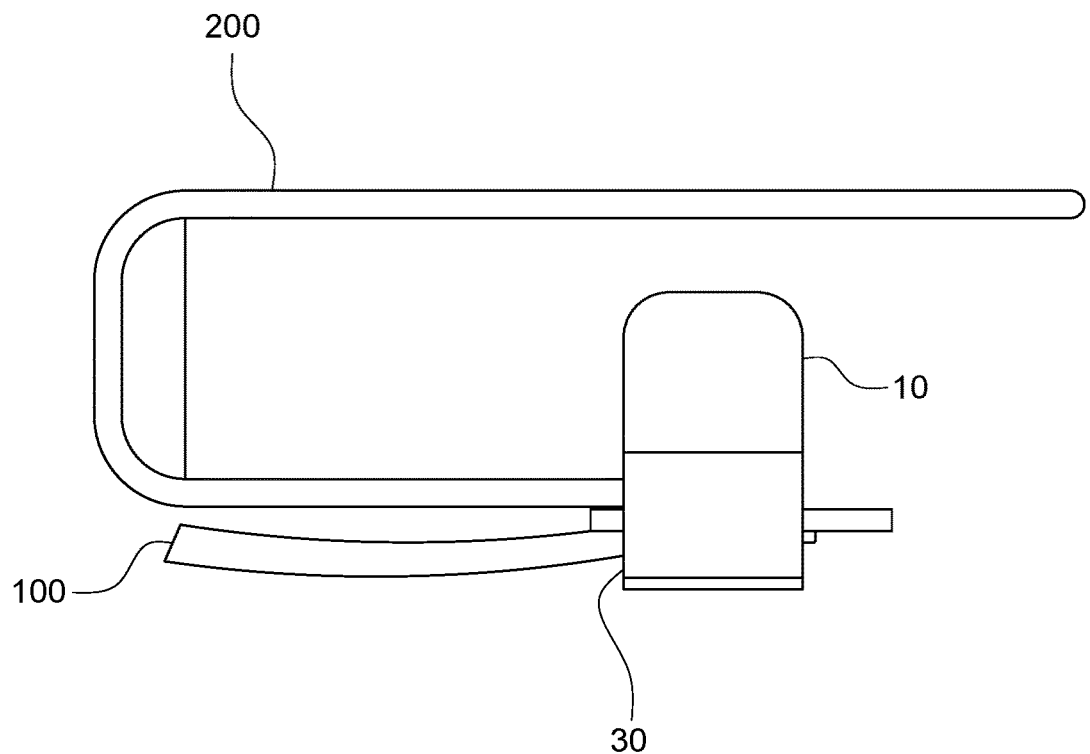
FIG. 15A is a side view of an alternative embodiment of the invention installed on an aimer ring with a sensor without a barrier sheath.
Figure 15B:
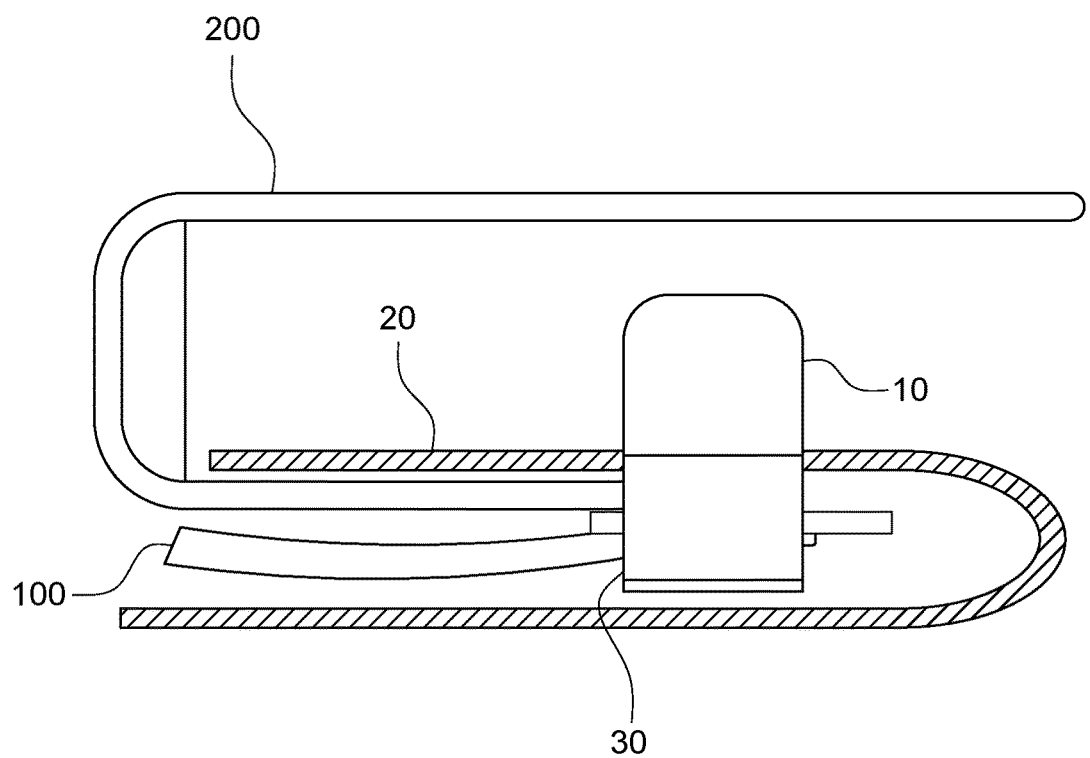
FIG. 15B is a side view of an alternative embodiment of the invention installed on an aimer ring with a sensor and with a barrier sheath in cross-section.
Figure 16:
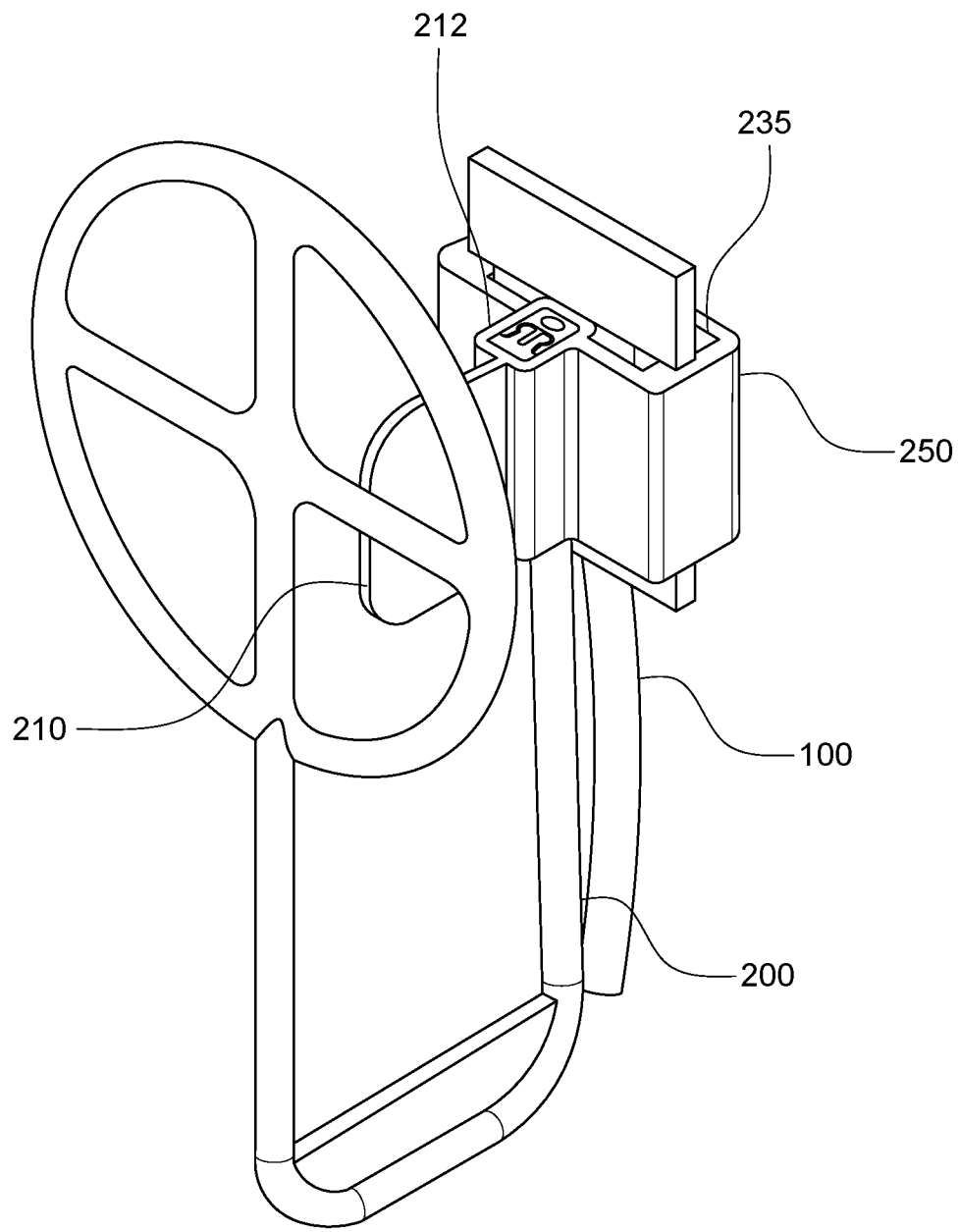
FIG. 16 is a perspective view of an alternative embodiment of the invention installed on an aimer ring without a barrier sheath.

Referring now to FIGS. 15A and 15B, a preferred embodiment is shown with the barrier sheath 20 in place in FIG. 15B and without the barrier sheath 20 in FIG. 15A. As shown in FIG. 15B, the barrier sheath 20 preferably contains a sensor 100, the interior container 30 and an aimer ring attachment 200 while the exterior attachment 10 is attached to the interior container 30 outside the barrier sheath 20. The exterior attachment 10 preferably presses a portion of the barrier sheath 20 into the gapped attachment port 32 and is held in place by the snug fit. FIG. 16 shows a perspective view of a preferred embodiment with the aimer ring attachment 200 and sensor 100 in place with the flexible fork exterior attachment 15 in place in the gapped attachment port 32.

Figure 17:
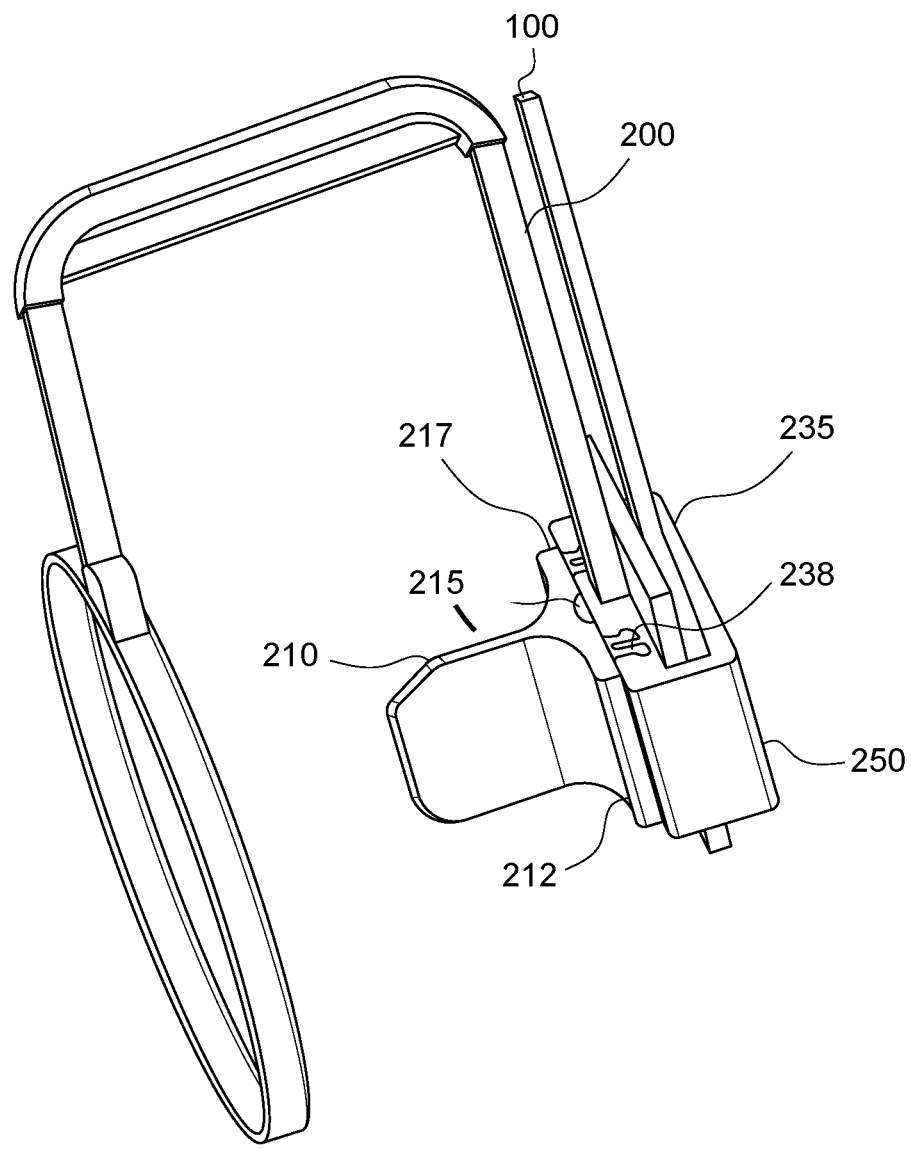
FIG. 17 is a perspective view of another alternative embodiment of the invention installed on an aimer ring with a sensor and without a barrier sheath.
Figure 18A:
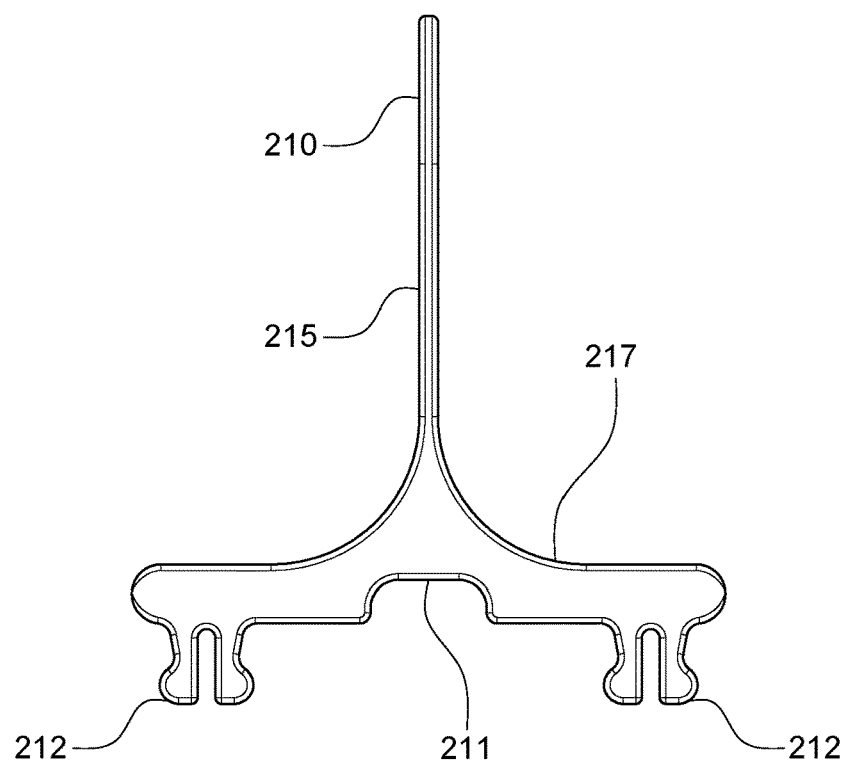
FIG. 18A is an end view of another alternative embodiment of an exterior attachment.
Figure 18B:
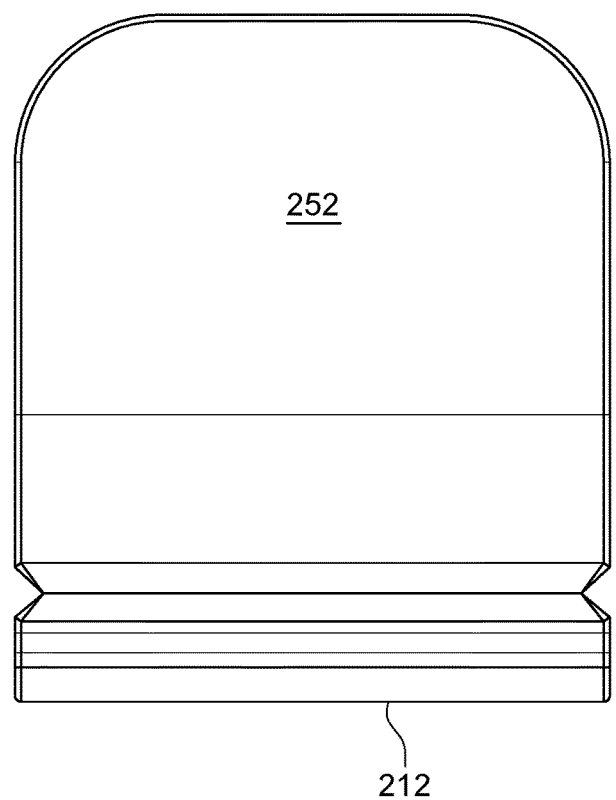
FIG. 18B is a side view of another alternative embodiment of an exterior attachment.

Referring now to FIG. 17, another preferred embodiment is shown. Again, the barrier sheath 20 is not shown for clarity. In FIG. 17, the exterior attachment 210 with bitewing 215 preferably has at least two male ridges 212 and a gapped attachment point 211. This preferred embodiment of the exterior attachment 10 is shown in FIGS. 18A and 18B. The male ridges 212 are preferably forked such as the male attachment point 15 in FIG. 10A. The male ridges 212 and gapped attachment point 211 interface with the preferred embodiment of interior container 230 shown in FIG. 17 and FIGS. 19A and 19B. The preferred embodiment of interior container 230 comprises a wider expansion slit 235, a portal for an aimer ring attachment 234, at least two attachment channels 236, and a male attachment point 238. As shown in FIGS. 17 and 18A and 18B, the exterior attachment 210 is shown with a bitewing 215 that slopes to a stabilizer block 217 that further preferably comprises the male ridges 212.

Figure 20A:
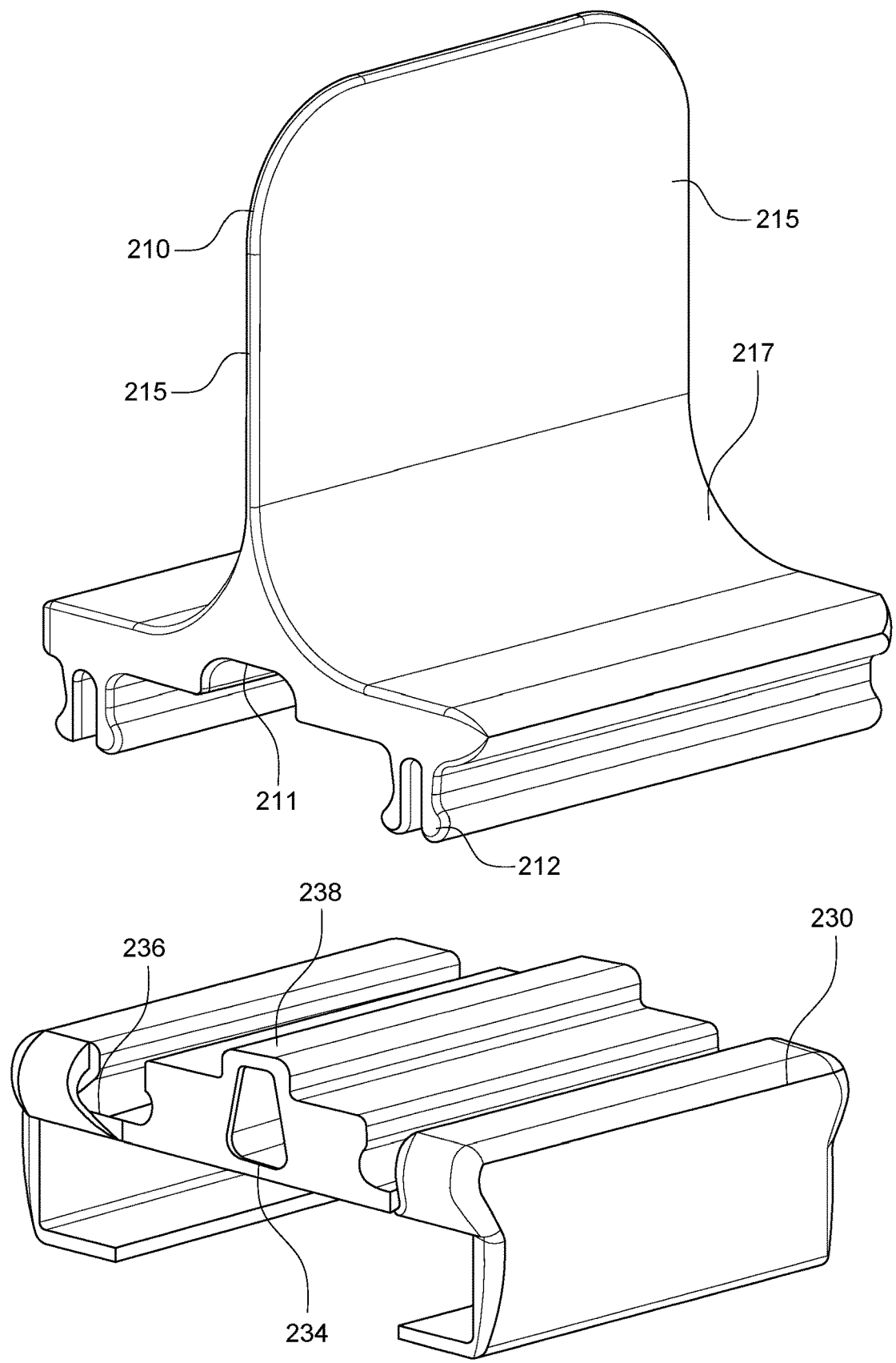
FIG. 20A is a side perspective exploded view of another alternative embodiment of the invention.
Figure 20B:
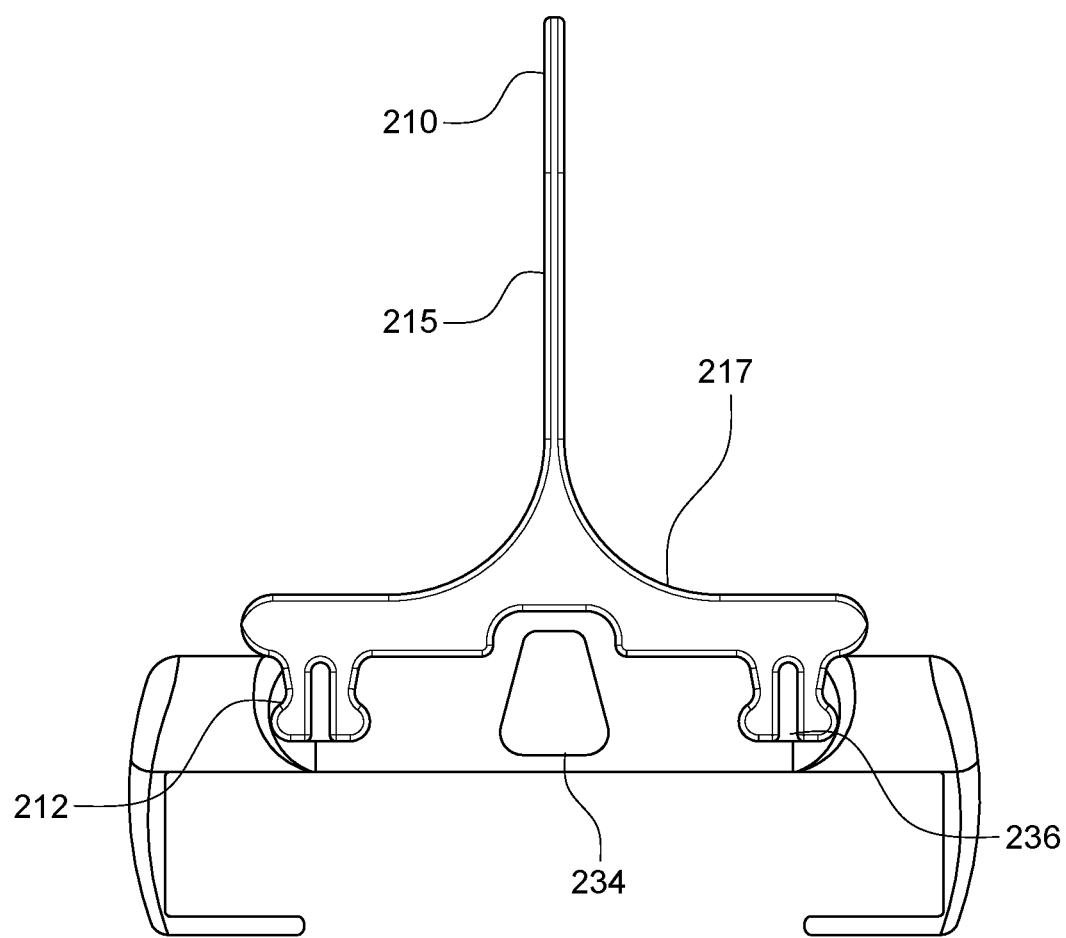
FIG. 20B is an end view of the embodiment from FIG. 20A.
Figure 21:
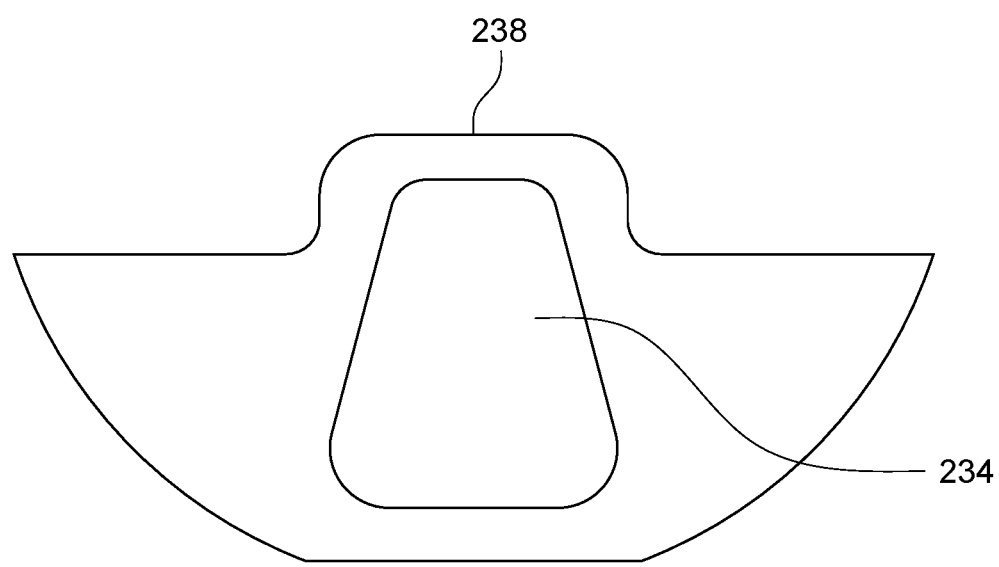
FIG. 21 is a partial end view of the embodiment of the sensor holder from FIG. 19A.
Figure 22:
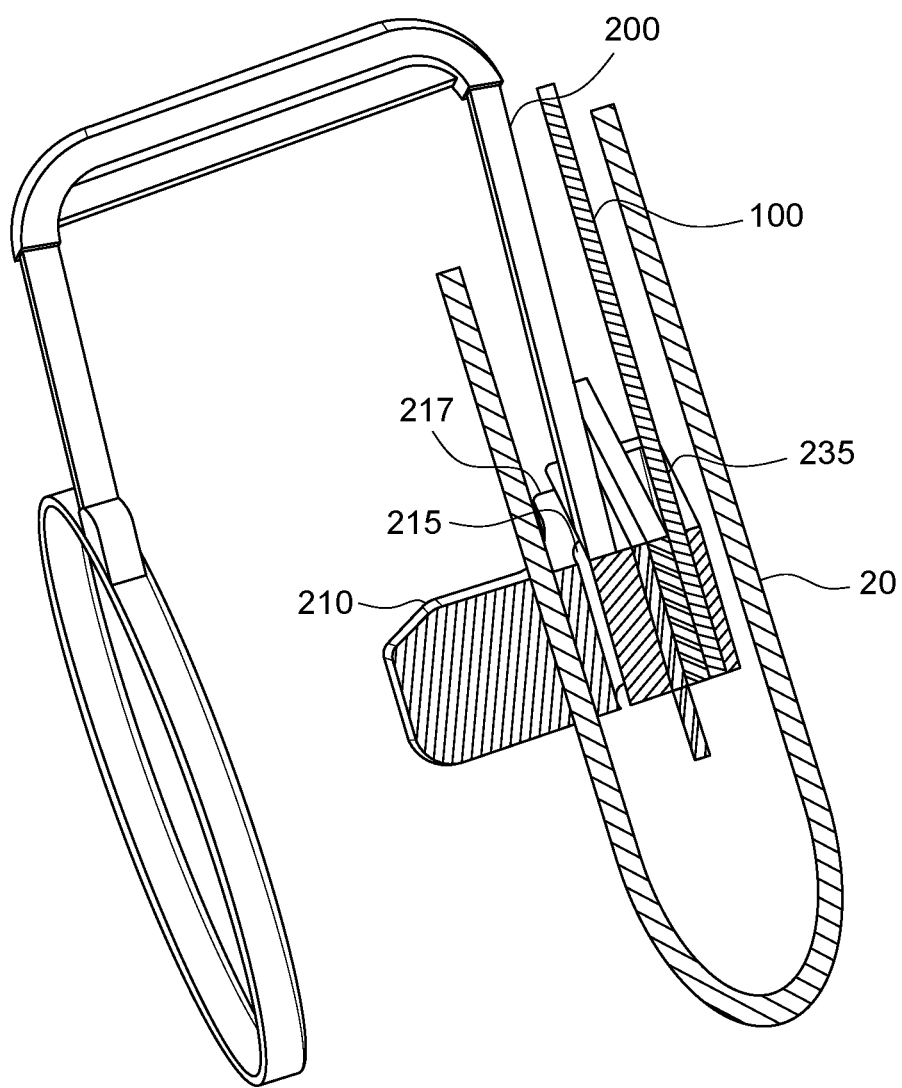
FIG. 22 is a side perspective view of another alternative embodiment of the invention installed on an aimer ring shown in cross-section with a barrier sheath and a sensor.

Referring now to FIGS. 20A and 20B, preferred embodiments of the exterior attachment 210 and the interior container 230 are shown separate (FIG. 20A) and attached (FIG. 20B). A close-up end view of a preferred embodiment of the portal for an aimer ring attachment 234 is shown in FIG. 21. FIG. 22 shows a side cross-sectional view of the preferred embodiment with a barrier 20 in place.

The alternative embodiments shown in FIGS. 9 to 22 inclusive lend themselves to the use of further "snap on" articles to allow for taking each of the images of a F.M.X. such as posterior, anterior, and vertical or "P.A.V." images while still keeping the sensor protected in a barrier sheath.

Figure 19A:
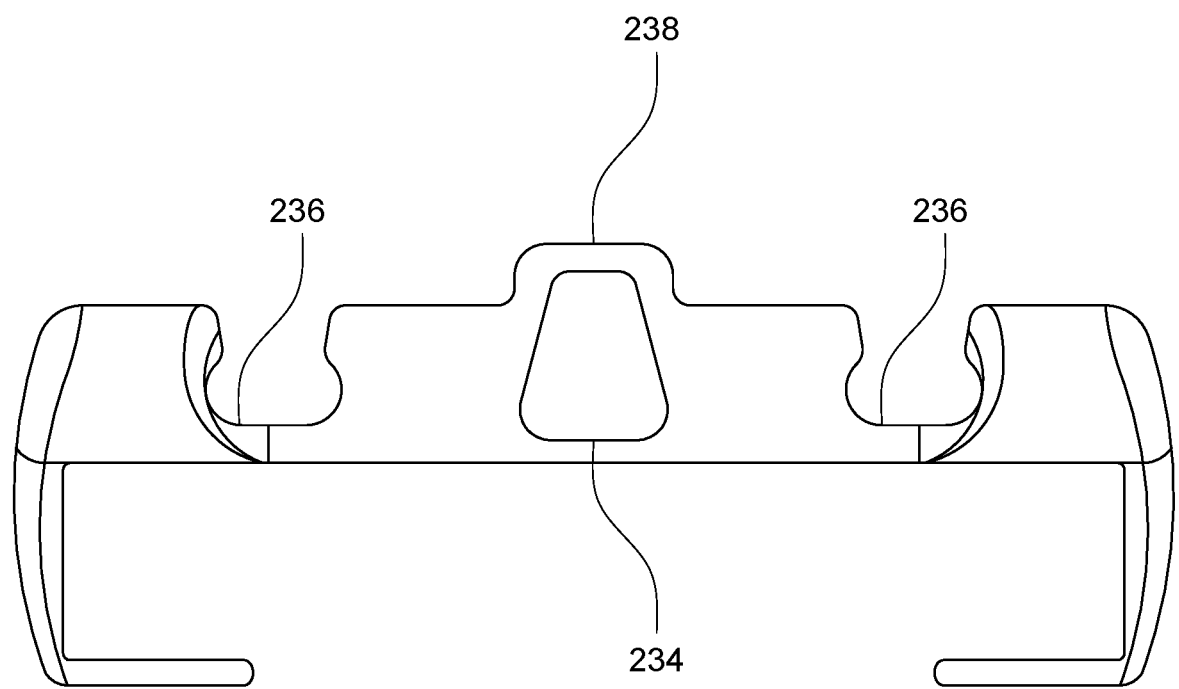
FIG. 19A is an end view of another alternative embodiment of a sensor holder.
Figure 19B:
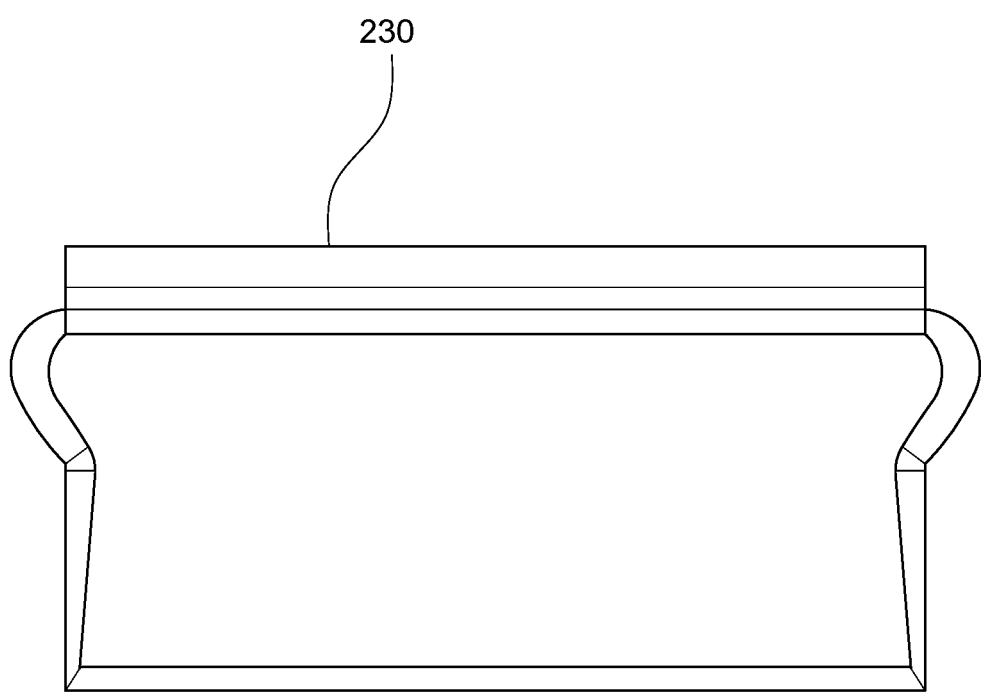
FIG. 19B is a side view of another alternative embodiment of a sensor holder.
Figure 23:
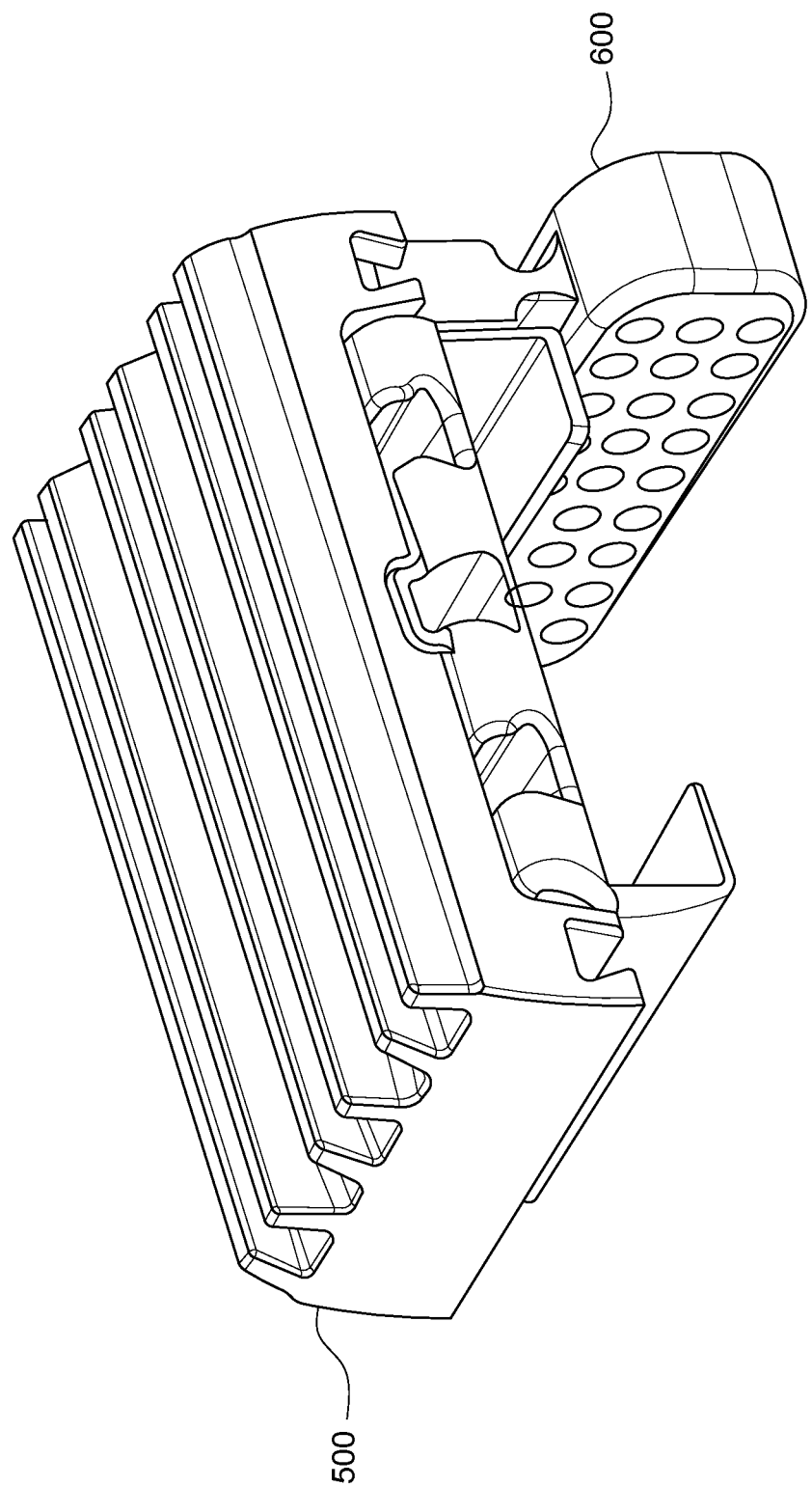
FIG. 23 is an end perspective view of an embodiment of snap-on articles.

Referring now to FIG. 23, a perspective view of preferred embodiments of snap on articles are shown attached to the interior container 230 (as seen in FIG. 19A). A PAV top 500 is shown attached to the interior container 230 at a gap attachment point 510. A bite block 600 is, in turn, attached to the PAV top 500. In practice, a barrier sheath 20 (not shown) encompasses the interior container 230 and a sensor 100 (not shown) with the PAV top 500 and bite block 600 external to the barrier sheath 20 with the sheath 20 compressed between the PAV top 500 and the interior container 230 at gap attachment point 510 and male attachment point 238.

Figure 24:
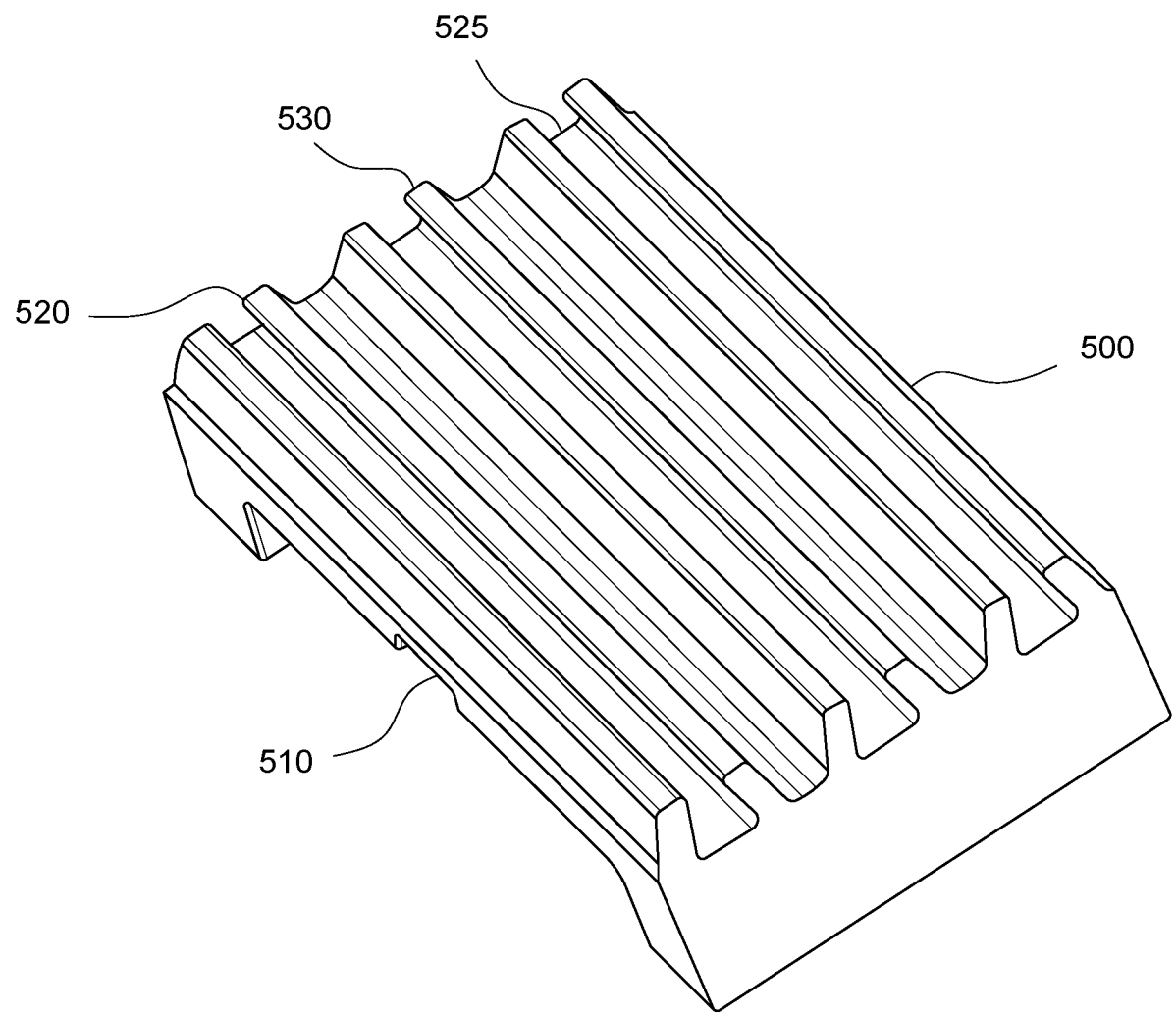
FIG. 24 is a top perspective view of an embodiment of a PAV top.

Referring now to FIG. 24, a top perspective view of the preferred PAV top 500 is shown. Preferably, the PAV top 500 comprises a first upper/lower anterior image groove 520 and a second upper/lower anterior image groove 525. Between these grooves 520, 525, there is preferably a vertical bite wing groove 530. These grooves 520, 525 and 530 allow for various bite wing attachment positions using, e.g., exterior attachment 210 (not shown).

Figure 25:
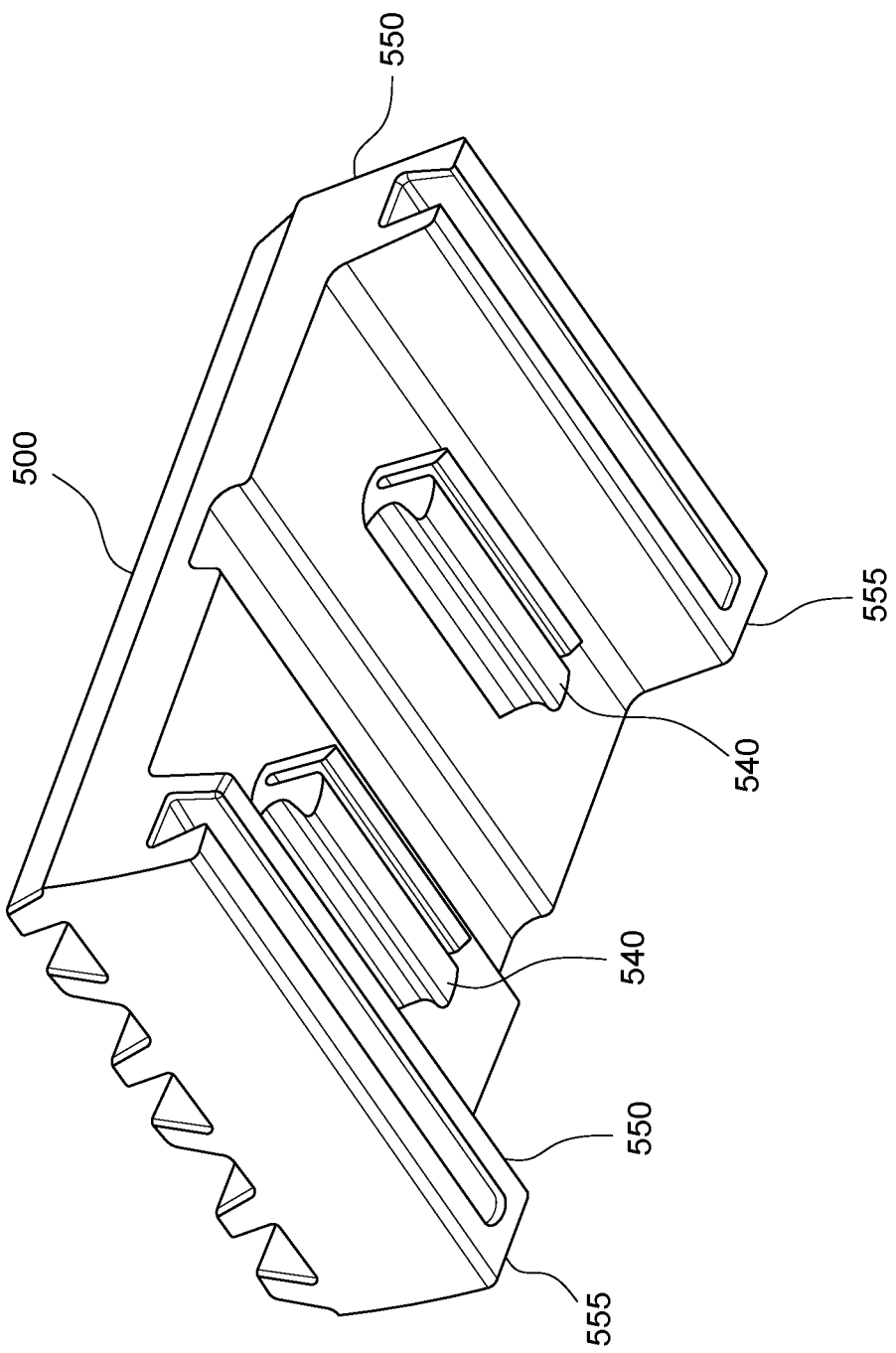
FIG. 25 is a bottom perspective view of an embodiment of a PAV top.

Referring now to FIG. 25, a bottom perspective view of the preferred PAV top 500 is shown. First and second male attachment points 540 are shown and are insertable into interior container 230 at attachment channels 236. The PAV top 500 further preferably comprises side grooves 550. The side grooves 550 are preferably used for right and left posterior image capture. Preferably, the side grooves 550 have "closed" ends 555 to allow for and guide proper positioning of bite block 600.

Figure 26:
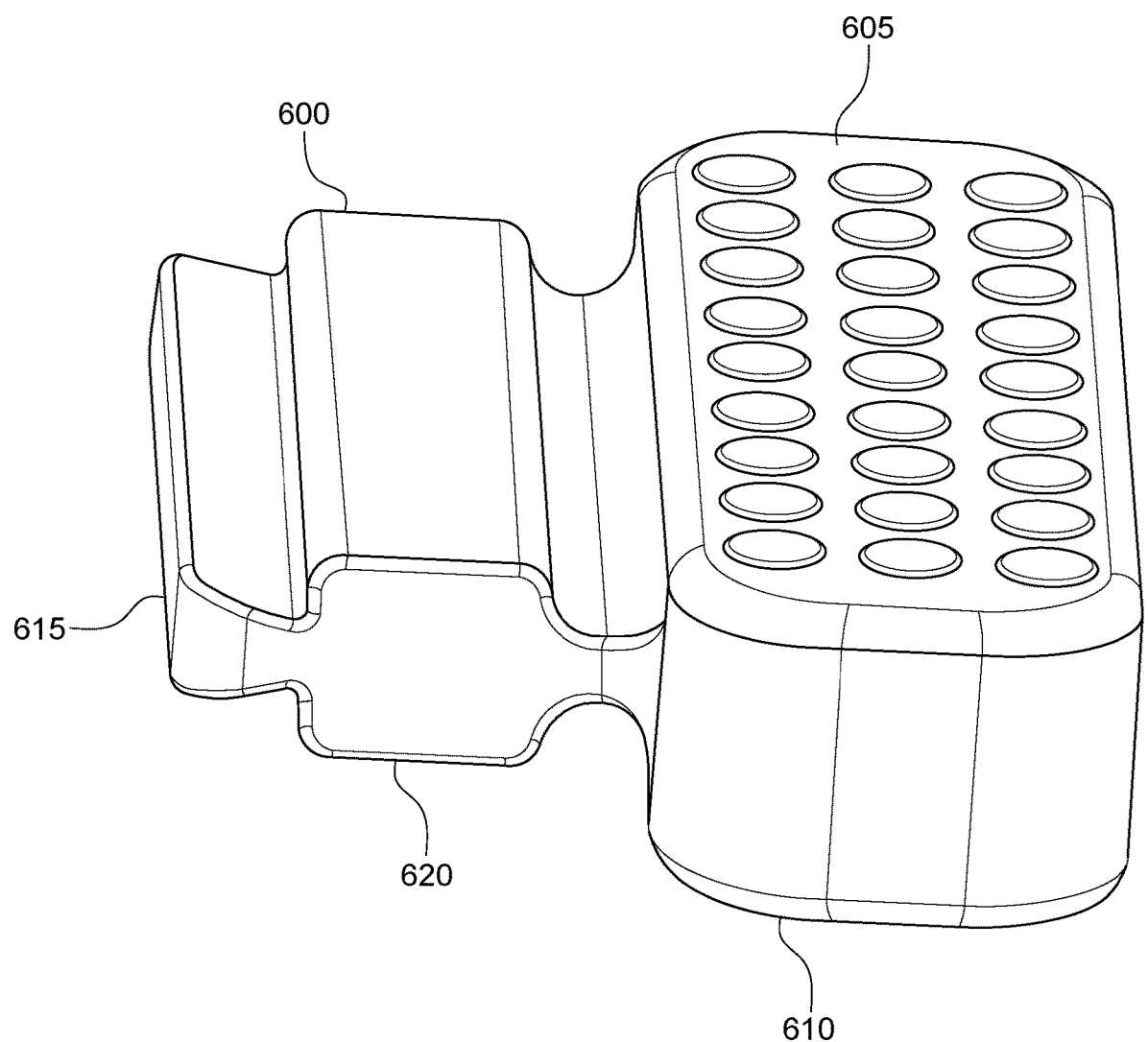
FIG. 26 is a side perspective view of an embodiment of a bite block.

Referring now to FIG. 26, a side perspective view of a preferred embodiment of the bite block 600 is shown. The bite block 600 preferably comprises a first textured bite surface 605 and a second textured bite surface 610. It also preferably comprises a bite block attachment point 615 for insertion into side grooves 550 of the PAV top 500. A stabilizing block 620 is preferably between the bite surfaces 605/610 and the bite block attachment point 615.

Figure 27A:
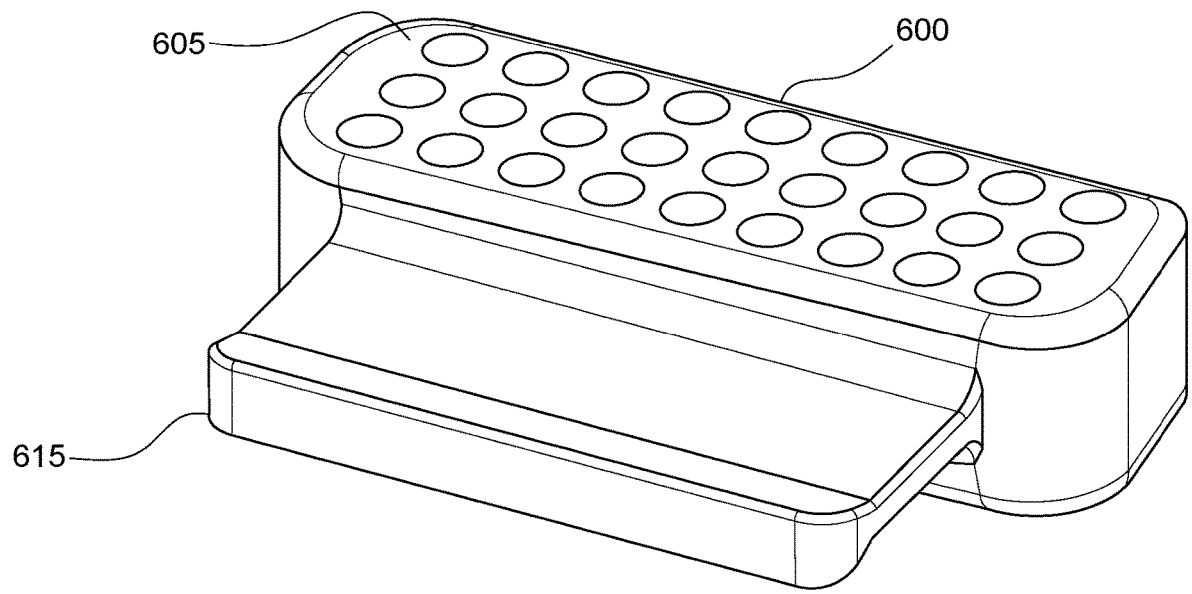
FIG. 27A is a side perspective view of another alternative embodiment of a bite block.
Figure 27B:
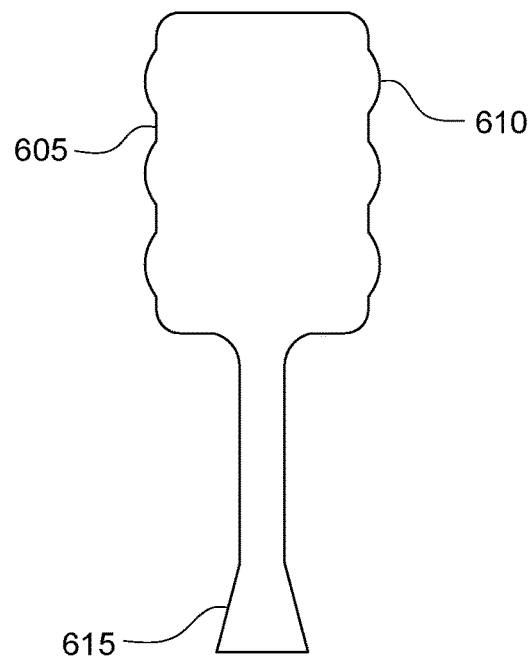
FIG. 27B is side cross-sectional view of the bite block in FIG. 27A.
Figure 27C:
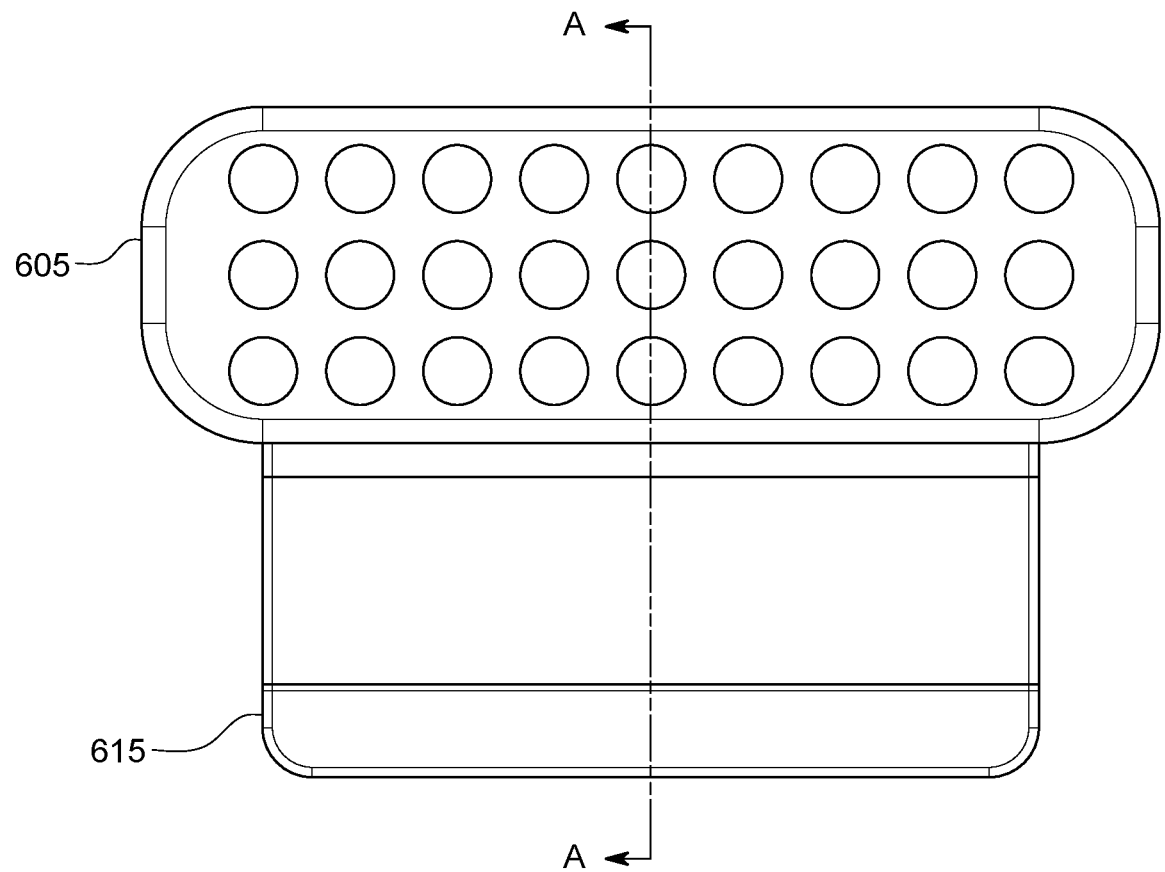
FIG. 27C is a top view of the bite block in FIG. 27A.
Figure 27D:
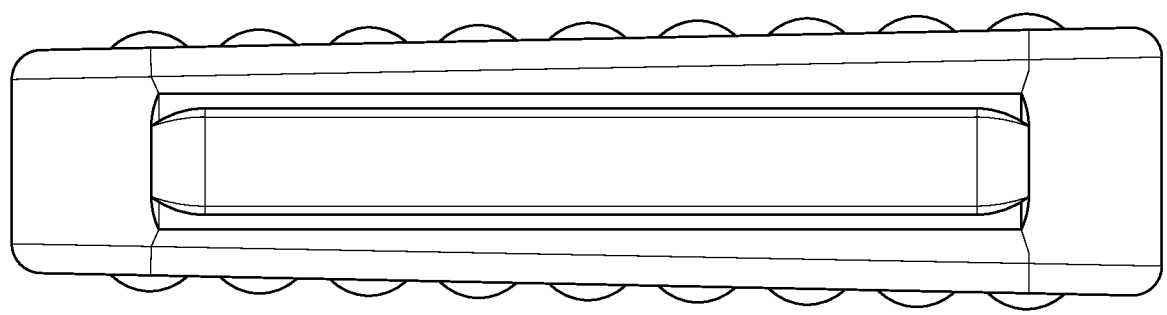
FIG. 27D is an end view of the bite block in FIG. 27A.

Referring now to FIGS. 27A, 27B, 27C and 27D, an alternate embodiment of the bite block 600 is shown. FIG. 27A is a side perspective view of a bite block 600 without a stabilizing block 620. FIG. 27B is a side cross-sectional view of the embodiment is FIG. 27A. FIG. 27C is a top view of the embodiment in FIG. 27A and FIG. 27D is an end view of the embodiment in FIG. 27A. In FIG. 27D, it shows that the first and second bite surfaces 605/610 preferably comprise a draft angle relative to the bite block attachment point 615. This draft angle is to compensate for the pan shape of a patient's oral cavity.

Figure 28:
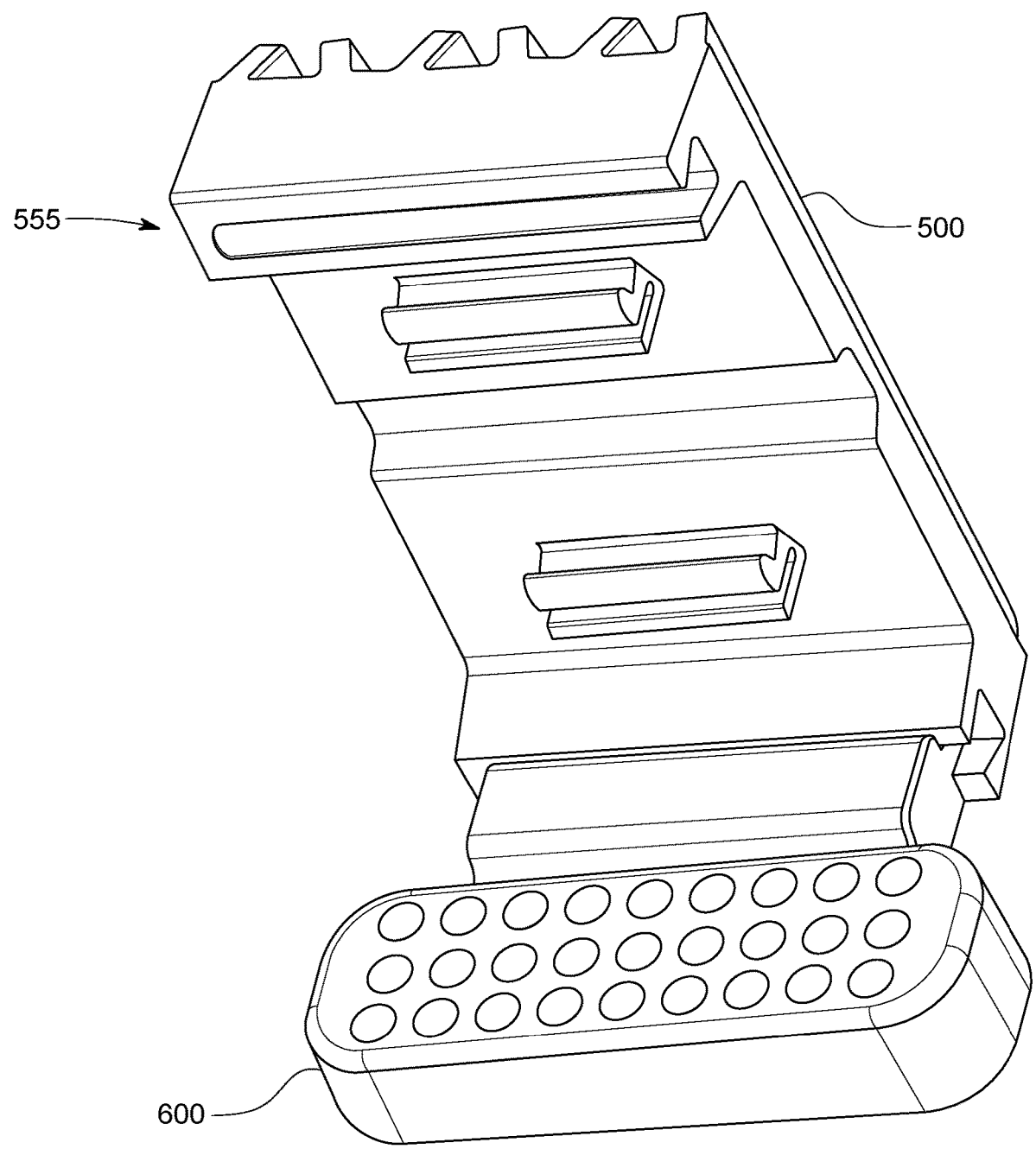
FIG. 28 is a perspective bottom view of another alternative embodiment of snap-on articles.

Referring now to FIG. 28, a perspective bottom view of a preferred embodiment of the snap on articles 500 and 600 is shown. As shown, the bite block 600 is inserted into the side groove 550 up to the closed end 555 to properly position the bite block 600.

Thus, an improved barrier-contained radiological sensor holder is described above that aids a dental practitioner in maintaining oral radiological sensors (regardless of size) in an uncontaminated state from patient to patient while providing a sensor positioning means for image capture and doing so in a more time efficient and cost-effective way than is currently available. In each of the above embodiments, the different positions and structures of the present invention are described separately in each of the embodiments. However, it is the full intention of the inventor of the present invention that the separate aspects of each embodiment described herein may be combined with the other embodiments described herein. Those skilled in the art will appreciate that adaptations and modifications of the just-described preferred embodiment can be configured without departing from the scope and spirit of the invention. Therefore, it is to be understood that, within the scope of the appended claims, the invention may be practiced other than as specifically described herein.

Various modifications and alterations of the invention will become apparent to those skilled in the art without departing from the spirit and scope of the invention, which is defined by the accompanying claims. It should be noted that steps recited in any method claims below do not necessarily need to be performed in the order that they are recited. Those of ordinary skill in the art will recognize variations in performing the steps from the order in which they are recited. In addition, the lack of mention or discussion of a feature, step, or component provides the basis for claims where the absent feature or component is excluded by way of a proviso or similar claim language.

While various embodiments of the present invention have been described above, it should be understood that they have been presented by way of example only, and not of limitation. Likewise, the various diagrams may depict an example architectural or other configuration for the invention, which is done to aid in understanding the features and functionality that may be included in the invention. The invention is not restricted to the illustrated example architectures or configurations, but the desired features may be implemented using a variety of alternative architectures and configurations. Indeed, it will be apparent to one of skill in the art how alternative functional, logical, or physical partitioning and configurations may be implemented to implement the desired features of the present invention. Also, a multitude of different constituent module names other than those depicted herein may be applied to the various partitions. Additionally, with regard to flow diagrams, operational descriptions and method claims, the order in which the steps are presented herein shall not mandate that various embodiments be implemented to perform the recited functionality in the same order unless the context dictates otherwise.

Although the invention is described above in terms of various exemplary embodiments and implementations, it should be understood that the various features, aspects and functionality described in one or more of the individual embodiments are not limited in their applicability to the particular embodiment with which they are described, but instead may be applied, alone or in various combinations, to one or more of the other embodiments of the invention, whether or not such embodiments are described and whether or not such features are presented as being a part of a described embodiment. Thus the breadth and scope of the present invention should not be limited by any of the above-described exemplary embodiments.

Terms and phrases used in this document, and variations thereof, unless otherwise expressly stated, should be construed as open ended as opposed to limiting. As examples of the foregoing: the term "including" should be read as meaning "including, without limitation" or the like; the term "example" is used to provide exemplary instances of the item in discussion, not an exhaustive or limiting list thereof; the terms "a" or "an" should be read as meaning "at least one," "one or more" or the like; and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that may be available or known now or at any time in the future. Likewise, where this document refers to technologies that would be apparent or known to one of ordinary skill in the art, such technologies encompass those apparent or known to the skilled artisan now or at any time in the future.

A group of items linked with the conjunction "and" should not be read as requiring that each and every one of those items be present in the grouping, but rather should be read as "and/or" unless expressly stated otherwise. Similarly, a group of items linked with the conjunction "or" should not be read as requiring mutual exclusivity among that group, but rather should also be read as "and/or" unless expressly stated otherwise. Furthermore, although items, elements or components of the invention may be described or claimed in the singular, the plural is contemplated to be within the scope thereof unless limitation to the singular is explicitly stated.

The presence of broadening words and phrases such as "one or more," "at least," "but not limited to" or other like phrases in some instances shall not be read to mean that the narrower case is intended or required in instances where such broadening phrases may be absent. The use of the term "module" does not imply that the components or functionality described or claimed as part of the module are all configured in a common package. Indeed, any or all of the various components of a module, whether control logic or other components, may be combined in a single package or separately maintained and may further be distributed across multiple locations.

As will become apparent to one of ordinary skill in the art after reading this document, the illustrated embodiments and their various alternatives may be implemented without confinement to the illustrated examples. For example, block diagrams and their accompanying description should not be construed as mandating a particular architecture or configuration.

The previous description of the disclosed embodiments is provided to enable any person skilled in the art to make or use the present invention. Various modifications to these embodiments will be readily apparent to those skilled in the art, and the generic principles defined herein may be applied to other embodiments without departing from the spirit or scope of the invention. Thus, the present invention is not intended to be limited to the embodiments shown herein but is to be accorded the widest scope consistent with the principles and novel features disclosed herein.

What is claimed is:

1. A barrier-contained radiological sensor holder comprising:
    a sensor holder and a barrier sheath having a closed end and an open end;
    the sensor holder comprising an exterior attachment and an interior container;
    the interior container having a gapped attachment port; where the interior container is located inside the barrier sheath between the open end and the closed end;
    the exterior attachment having a male attachment point that is inserted into the gapped attachment port pressing a portion of the barrier sheath into the gapped attachment port.

2. The barrier-contained radiological sensor holder of claim 1 where the barrier sheath comprises elastomer latex material.

3. The barrier-contained radiological sensor holder of claim 1 where the barrier sheath comprises flexible or elastic plastic material.

4. The barrier-contained radiological sensor holder of claim 1 where the exterior attachment is a bite surface.

5. The barrier-contained radiological sensor holder of claim 3 where the exterior attachment is a bitewing.

6. The barrier-contained radiological sensor holder of claim 1 where the barrier sheath has a thickness of 0.001 to 0.004 inches.

7. The barrier-contained radiological sensor holder of claim 1 where the barrier sheath has an elongation between 400 and 1000 percent and a durometer between 20 Shore 00 and 30 Shore D.

8. The radiological sensor holder of claim 1 where the interior container further comprises a port for an aimer ring.

9. A barrier-contained radiological sensor holder comprising:
    a sensor holder and a barrier sheath having a closed end and an open end;
    the sensor holder comprising an exterior attachment and an interior container;
    the interior container having a male attachment point; where the interior container is located inside the barrier sheath between the open end and the closed end;
    the exterior attachment having a gapped attachment point that is placed onto the male attachment point pressing a portion of the barrier sheath into the gapped attachment port.

10. A barrier-contained radiological sensor holder comprising:
    a sensor holder and a barrier sheath having a closed end and an open end;
    the sensor holder comprising an exterior attachment and an interior container;
    the interior container having at least two attachment channels and a male attachment point; where the interior container is located inside the barrier sheath between the open end and the closed end; and,
    the exterior attachment having a gapped attachment point and at least two male ridges; where the gapped attachment point is placed onto the male attachment point pressing a first portion of the barrier sheath into the gapped attachment port and the at least two male ridges are placed into the at least two attachment channels with at least a second and third portion of the barrier sheath pressed into the at least two attachment channels.

11. The radiological sensor holder of claim 10 where the interior container further comprises a port for an aimer ring.

12. The radiological sensor holder of claim 11 where the exterior attachment is a bite surface.

13. The barrier-contained radiological sensor holder of claim 11 where the exterior attachment is a bitewing.

14. The radiological sensor holder of claim 10 where the barrier sheath comprises elastomer latex material.

15. The radiological sensor holder of claim 10 where the barrier sheath has an elongation between 400 and 1000 percent and a durometer between 20 Shore 00 and 30 Shore D.

16. The radiological sensor holder of claim 10 where the interior container further comprises an expansion slit.

17. The radiological sensor holder of claim 10 further comprising a PAV top having a top side and a bottom side; the top side having a plurality of grooves for the exterior attachment and the bottom side having a first and second PAV male attachment points for connection to the interior container.

18. The radiological sensor holder of claim 17 further comprising a bite block and where the PAV top further comprises two closed-end side grooves, either groove containing the bite block.

* * * * *